US006168932B1

(12) United States Patent
Uckun et al.

(10) Patent No.: US 6,168,932 B1
(45) Date of Patent: Jan. 2, 2001

(54) RECOMBINANT $DT_{CT}$GMCSF FUSION TOXIN IN A BACULOVIRUS EXPRESSION VECTOR SYSTEM

(75) Inventors: Fatih M. Uckun, White Bear Lake; Mark D. Williams, St. Paul; Alexander Rostovstev, Maplewood, all of MN (US)

(73) Assignee: Parker Hughes Institute, Roseville, MN (US)

( * ) Notice: Under 35 U.S.C. 154(b), the term of this patent shall be extended for 0 days.

(21) Appl. No.: 09/114,503

(22) Filed: Jul. 13, 1998

(51) Int. Cl.[7] .......................... C12N 15/62; C12N 15/63; C12N 15/27; C07K 19/00; C07K 14/54

(52) U.S. Cl. ...................... 435/69.7; 435/71.1; 435/71.3; 435/471; 435/252.3; 435/348; 435/320.1; 530/412; 530/416

(58) Field of Search ................................ 435/69.7, 71.1, 435/71.3, 471, 252.3, 348, 320.1; 530/412, 416

(56) References Cited

FOREIGN PATENT DOCUMENTS

WO 96/38571 * 12/1996 (WO) .

OTHER PUBLICATIONS

Arceci, R. J., "Clinical Significance of P–Glycoprotein in Multidrug Resistance Malignancies [editorial] [see comments]", *Blood,* 81, 2215–2222 (1993).*

Au, L. C., et al., "Secretory Production of Bioactive Recombinant Human Granulocyte– Macrophage Colony Stimulating Factor by a Baculovirus Expression System", *J. Biotechnol,* 51, 107–113 (1996).*

Bendel, A. E., et al., "A Recombinant Fusion Toxin Targeted to the Granulocyte–Macrophage Colony–Stimulating Factor Receptor" *Leuk Lymphoma,* 25, 257–270 (1997).*

Bradford, M. M., "A Rapid and Sensitive Method for the Quantitation of Microgram Quantities of Protein Utilizing the Principle of Protein–Dye Binding", *Anal Biochem.,* 72, 248–254 (1976).*

Brocks, B., "A TNF Receptor Antagonistic scFv, Which is Not Secreted in Mammalian Cells, is Expressed as a Soluble Mono– and Bivalent scFv Derivative in Insect Cells", *Immunotechnology.,* 3, 173–184 (1997).*

Chan, H. S., et al., "Multidrug Resistance. Clinical Opportunities in Diagnosis and Circumvention", *Hematol Oncol Clin North Am.,* 8, 383–410 (1994).*

Chiou, C. J., et al., "Expression of Human Granulocyte–Macrophage Colony–Stimulating Factor Gene in Insect Cells by a Baculovirus Vector". *FEBS Lett,* 259, 249–253 (1990).*

Collins, S. J., "The HL–60 Promyelocytic Leukemia Cell Line: Proliferation, Differentiation, and Cellular Oncogene Expression", *Blood* 70, 1233–1244 (1987).*

Espevik, T., et al., "A Highly Sensitive Cell Line, WEHI 164 Clone 13, for Measuring Cytotoxic Factor/Tumor Necrosis Factor from Human Monocytes", *J Immunol Methods,* 95, 99–105 (1986).*

Frankel, A. E., "Characterization of a Ricin Fusion Toxin Targeted to the Interleukin–2 Receptor", *Protein Eng.,* 9, 913–919 (1996).*

Frankel, A., et al., "IL2–Ricin Fusion Toxin is Selectively Cytotoxic In Vitro to IL2 Receptor–Bearing Tumor Cells", *Bioconjug Chem.,* 6, 666–672 (1995).*

Fraser, A., et al., "A License to Kill", *Cell.,* 85, 781–784 (1996).*

Green, L. M., et al., "Rapid Colorimetric Assay for Cell Viability: Application to the Quantitation of Cytotoxic and Growth Inhibitory Lymphokines", *J Immunol Methods,* 70, 257–268 (1984).*

Griffiths, C. M., et al., "Production of Heterologous Proteins Using the Baculovirus/Insect Expression System", *Methods Mol Biol.,* 75, 427–440 (1997).*

Jean, L. F., et al., "Diphtheria Toxin Receptor–Binding Domain Substitution With Interleukin 6: Genetic Construction and Interleukin 6 Receptor–Specific Action of a Diphtheria Toxin–Related Interleukin 6 Fusion Protein", *Protein Eng.*4, 989–994 (1991).*

Jones, I., et al., "Baculovirus Vectors for Expression in Insect Cells", *Curr Opin Biotechnol.,* 7, 512–516 (1996).*

Kool, M., et al., "Detection and Analysis of *Autographa Californica* Nuclear Polyhedrosis Virus Mutants with Defective Interfering Properties", *Virology,* 183, 739–746 (1991).*

Kretzchmar, T., "High–Level Expression in Insect Cells and Purification of Secreted Monomeric Single–Chain Fv Antibodies", *J Immunol Methods* 195, 93–101 .(1996).*

Lakkis, F., et al., "Interleukin 4 Receptor Targeted Cytotoxicity: Genetic Construction and In Vivo Immunosuppressive Activity of a Diphtheria Toxin–Related Murine Interleukin 4 Fusion Protein", *Eur J Immunol.* 21, 2253–2258 (1991).*

Langridge, J., et al. "Extraction of Nucleic Acids from Agarose Gels", *Anal Biochem.,* 103, 264–271 (1980).*

LeMaistre, C. F., et al., "Phase I Trial of a 90–Minute Infusion of the Fusion Toxin DAB486IL–2 in Hematological Cancers", *Cancer Res.,* 53, 3930–3934 (1993).*

LeMaistre, C. F., et al., "Phase I Trial of a Ligand Fusion––Protein (DAB389IL–2) in Lymphomas Expressing the Receptor for Interleukin–2", *Blood.,* 91, 399–405 (1998).*

LeMaistre, C. F., et al., "Phase I Trial of an Interleukin–2 (IL–2) Fusion Toxin (DAB486IL–2) in Hematologic Malignancies Expressing the EL–2 Receptor", *Blood,* 79, 2547–2554 (1992).*

(List continued on next page.)

*Primary Examiner*—Prema Mertz
*Assistant Examiner*—Fozia Hamud
(74) *Attorney, Agent, or Firm*—Merchant & Gould P.C.

(57) ABSTRACT

A soluble form of $DT_{ct}$GMCSF is produced with high yield in insect cells, preferably using the baculovirus expression vector system (BEVS).

15 Claims, 12 Drawing Sheets

OTHER PUBLICATIONS

Luckow, V. A., et al., "Efficient Generation of Infectious Recombinant Baculoviruses by Site–Specific Transposon–Mediated Insertion of Foreign Genes into a Baculovirus Genome Propagated in *Escherichia coli*", *J Virol.*, 67, 4566–4579 (1993).*

McCarthy, N. J., et al., "Methods for Detecting and Quantifying Apoptosis", *Curr Top Dev Biol.*, 36, 259–278 (1998).*

Medin, J.A. et al., "Efficient, Low–Cost Protein Factories: Expression of Human Adenosine Deaminase in Baculovirus–Infected Insect Larvae", *Proc. Natl. Acad. Sci. USA*, 87, 2760–2764, (Apr. 1990).*

Meneghetti, C. M., et al., "Initial Clinical Experiences With an Interleukin–2 Fusion Toxin (DAB486–IL–2)", *Targeted Diagn Ther.*, 7, 395–401 (1992).*

Murhammer, D.W., "The Use of Insect Cell Cultures for Recombinant Protein Synthesis: Engineering Aspects", *Applied Biochemistry and Biotechnology*, vol. 31, p. 283–310 (1991).*

Murphy, J. R., et al., "Genetic Construction, Expression, and Melanoma–Selective Cytotoxicity of a Diphtheria Toxin–Related Alpha–Melanocyte–Stimulating Hormone Fusion Protein", *Proc Natl Acad Sci USA*, 83, 8258–8262 (1986).*

Musto, P., et al., "High Risk of Early Resistant Relapse for Leukaemic Patients With Presence of Multidrug Resistance Associated P–Glycoprotein Positive Cells in Complete Remission" *Br J Haematol*, 77, 50–53 (1991).*

Myers, D. E., et al., "Membrane–Associated CD19–LYN Complex is an Endogenous p53–Independent and Bcl–2–independent Regulator of Apoptosis in Human B–lineage Lymphoma Cells", *Proc Natl Acad Sci USA*, 92, 9575–9579 (1995).*

Pennock, G.D. et al., "Strong and Regulated Expression of *Escherichia coli* β–Galactosidase in Insect Cells with a Baculovirus Vector", *Molecular and Cellular Biology*, vol. 4 No. 3, p. 399–406 (Mar. 1984).*

Perentesis, J. P., et al. "Induction of Apoptosis in Multidrug Resistant and Radiation–Resistant Acute Myeloid Leukemia Cells by a Recombinant Fusion Toxin Directed Against the Human Granulocyte Macrophage Colony Stimulating Factor Receptor", *Clinical Cancer Research*, 3, 347–355 (1997).*

Perentesis, J. P., et al., "Granulocyte–Macrophage Colony–Stimulating Factor Receptor–Targeted Therapy of Chemotherapy– and Radiation–Resistant Human Myeloid Leukemias", *Leuk Lymphoma*, 25, 247–256 (1997).*

Perentesis, J. P., et al., "In vivo Biotherapy of HL–60 Myeloid Leukemia With a Genetically Engineered Recombinant Fusion Toxin Directed Against the Human Granulocyte Macrophage Colony Stimulating Factor Receptor", *Clinical Cancer Research*, 3, 2217–2227 (1997).*

Pirker, R., et al., "MDR1 Gene Expression and Treatment Outcome in Acute Myeloid Leukemia", *J. Natl. Cancer Inst. (Bethesda)*, 708–712 (1991).*

Possee, R. D., "Baculoviruses as Expression Vectors", *Curr Opin Biotechnol.*, 8, 569–572 (1997).*

Rivas, C. I., et al., "Expression of Granulocyte–Macrophage Colony–Stimulating Factor Receptors in Human Prostate Cancer", *Blood.*,91, 1037–1043 (1998).*

Sato, H., et al., "MDR1 Transcript Levels as an Indication of Resistant Disease in Acute Myelogenous Leukaemia", *Br J Haematol*, 75, 340–345 (1990).*

Schiffer, C. A. "Acute Myeloid Leukemia in Adults", *Cancer Medicine*, 1907–1933 (1993).*

Shaw, J. P., et al., "Cytotoxic Properties of DAB486EGF and DAB389EGF, Epidermal Growth Factor (EGF) Receptor–Targeted Fusion Toxins", *J Biol Chem.*, 266, 21118–21124 (1991).*

Steller, H., "Mechanisms and Genes of Cellular Suicide". *Science*, 267, 1445–1449 (1995).*

Thompson, C. B., "Apoptosis in the Pathogenesis and Treatment of Disease", *Science*, 267, 1456–1462 (1995).*

Uckun, F. M., et al., "Biotherapy of B–cell Precursor Leukemia by Targeting Genistein to CD 19–Associated Tyrosine Kinases", *Science*, 267, 886–891 (1995).*

Uckun, F. M., et al., "Ionizing Radiation Stimulates Unidentified Tyrosine–Specific Protein Kinases in Human B–lymphocyte Precursors, Triggering Apoptosis and Clonogenic Cell Death", *Proc Natl Acad Sci USA*, 89, 9005–9009 (1992).*

Vaughn, J. L., et al., "The Establishment of Two Cell Lines From the Insect *Spodoptera Frugiperda* (Lepidoptera, Noctuidae)", *In Vitro.*, 13, 213–217 (1977).*

Volkman, L. E., "Baculovirus bounty", *Science.*, 269, 1834 (1995).*

Williams, D. P., "Diphtheria Toxin Receptor Binding Domain Substitution With Interleukin–2: Genetic Construction and Properties of a Diphtheria Toxin–related Interleukin–2 Fusion Protein", *Protein Eng*, 1, 493–498 (1987).*

Williams, M. D., et al., "Expression and Analysis of a Bacterial Poly(hydroxyalkanoate) Synthase in Insect Cells using a Baculovirus System", *Protein Expr Purif.*, 7, 203–211 (1996).*

Williams, M.D. et al., "Production of a Polyhydroxyalkanoate Biopolymer in Insect Cells with a Modified Eucaryotic Fatty Acid Synthase", *Applied and Environmental Microbiology*, 62, 2540–2546 (Jul. 1996).*

Maeda, Susma . Annual Review of Entomology, vol. 34, pp. 351–372. 1989.*

Awald et al. Biochemica et Biophysica Acta, vol. 1201, pp. 312–320. 1994.*

* cited by examiner

FIG. 3A
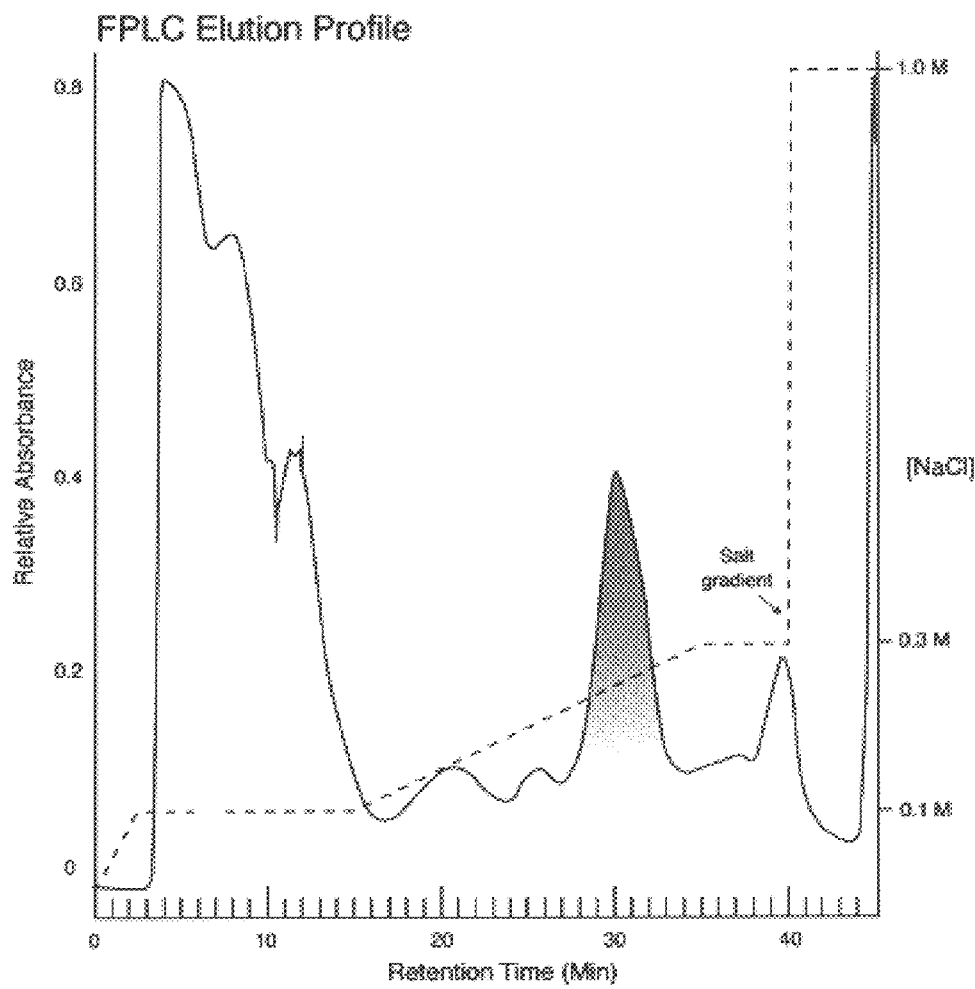
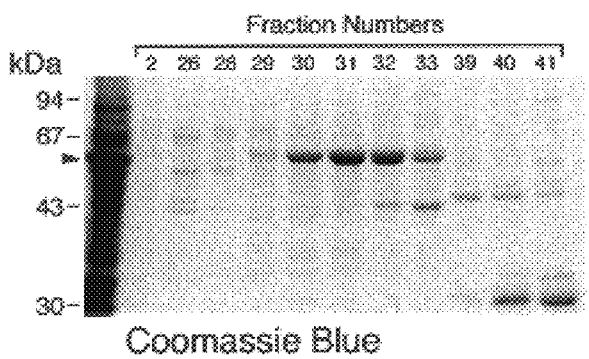
FIG. 3B
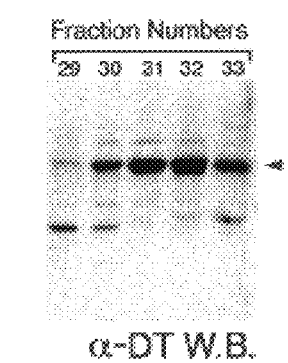
FIG. 3C

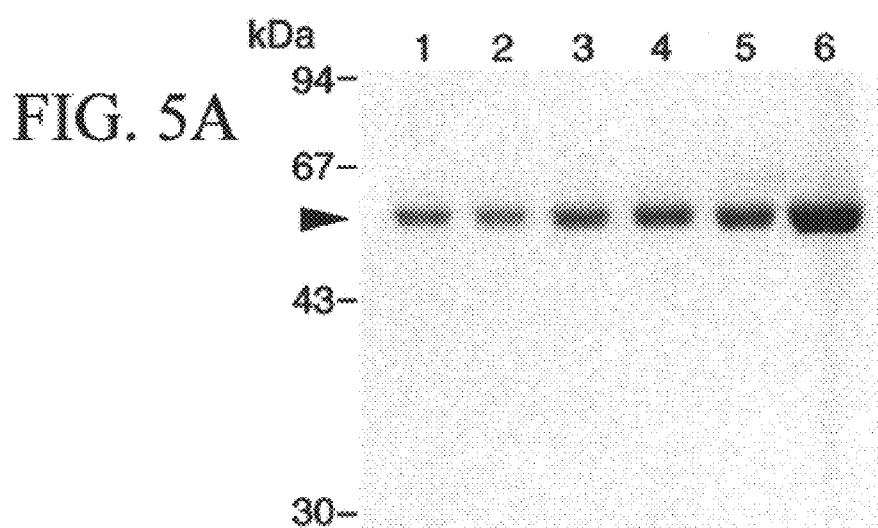
FIG. 5A Coomassie Blue
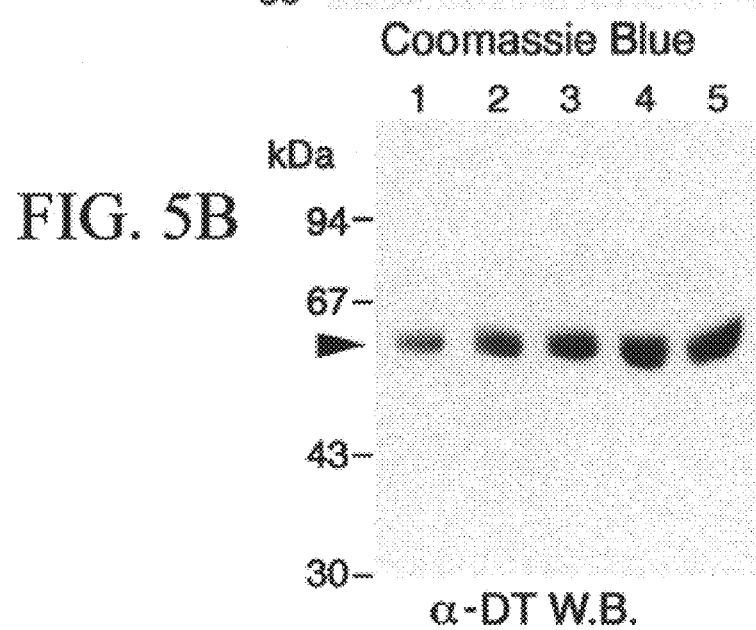
FIG. 5B α-DT W.B.
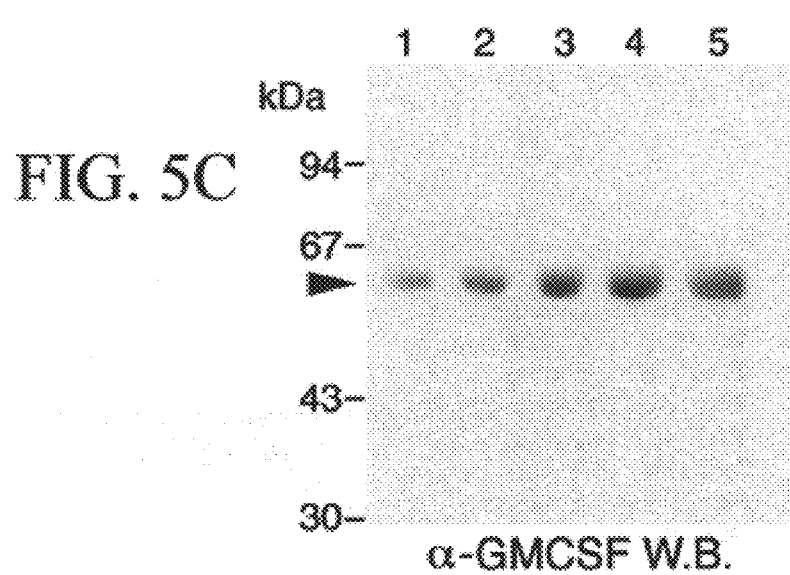
FIG. 5C α-GMCSF W.B.

Fluorescence Intensity

RECOMBINANT DT$_{CT}$-GMCSF FUSION TOXIN IN A BACULOVIRUS EXPRESSION VECTOR SYSTEM

FIELD OF THE INVENTION

The present invention relates to compositions and methods for large scale production of a fusion toxin. In particular, the invention relates to the large scale production of diphtheria toxin fused to a moiety selected to target the toxin to a specific cell or tissue, such as a tumor cell.

BACKGROUND OF THE INVENTION

Acute myeloid leukemia (AML) is the most common form of leukemia found in adults and the second most common leukemia affecting children. Despite intensive multimodality treatment programs, including chemotherapy and bone marrow transplantation, more than one-half of patients with AML die because of therapy-refractory or recurrent leukemia. Consequently, the development of effective new agents capable of killing multidrug resistant leukemia cells has emerged as an exceptional focal point for translational research in treatment of AML.

Recombinant DNA technology is now used to generate fusion toxins, providing a means for producing these therapeutic biomolecules with consistent characteristics. For example, recombinant DNA techniques have been used to produce diphtheria toxin (DT) fused to targeting moieties including interleukin (IL)-2, IL-4, IL-6, epidermal growth factor (EGF), and the melanocyte-stimulating hormone (MSH) in order to target this toxin to specific tumor cells expressing the receptor for the targeting moiety. Clinical trials using DT$_{ct}$IL-2 fusion toxins have provided encouraging evidence for partial or complete remission of disease in patients with IL-2 receptor positive lymphoid malignancies.

DT$_{ct}$GMCSF is a genetically engineered recombinant fusion toxin that directs the lethal diphtheria toxin (DT) to high affinity granulocyte-macrophage colony stimulating factor (GMCSF) receptors (R) present on specific tumor cells, including, among others, AML cells. DT$_{ct}$GMCSF preserves the portions of DT that include the lethal catalytic ADP-ribosyltransferase domain (c domain) and the contiguous portion of DT that is associated with translocation across cellular membranes (t domain). The native receptor binding domain of DT is replaced with human GMCSF in the construction of the DT$_{ct}$GMCSF fusion toxin. The preparation and efficacy of a fusion toxin such as DT$_{ct}$GMCSF has been described, for example, in U.S. Pat. Nos. 5,744,580, 5,756,699, 5,677,274, and 5,681,810.

DT$_{ct}$GMCSF is selectively cytotoxic to a wide range of AML cells, including those with multidrug resistance. DT$_{ct}$-GMCSF induces rapid apoptotic death in chemotherapy-resistant AML cell lines and in primary leukemia cells from therapy-refractory AML patients. At nontoxic dose levels, DT$_{ct}$GMCSF is superior to standard chemotherapeutic agents such as ARA-C and adriamycin, resulting in 60% long-term survival of severe combined immunodeficient (SCID) mice challenged with an otherwise invariably fatal dose of xenografted human AML cells. Importantly, systemic exposure of cynomolgus monkeys to levels of DT$_{ct}$-GMCSF which were found to be therapeutic in the SCID mouse xenograft model of human AML, can be achieved without any significant nonhematological toxicity. Taken together, these preclinical studies indicate that DT$_{ct}$GMCSF fusion toxin has clinical potential for more effective treatment of therapy-refractory AML patients.

DT$_{ct}$GMCSF is selectively cytotoxic to GMCSF receptor (R) positive acute myeloid leukemia (AML) cells both in vitro and in vivo (see for example, Perentesis et al., 1997, Clinical Cancer Research, 3:347–355; and Perentesis et al., 1997, Clinical Cancer Research, 3:2217–2227), however, its clinical development has been hampered by the inability to produce large amounts of the cytotoxin in traditional host cell systems. Previous expression attempts have resulted in very low expression levels, requirements for solubilization with guanidine hydrochloride and subsequent refolding, and concerns about bacterial endotoxin contamination. In addition, DT$_{ct}$GMCSF is toxic to most cellular hosts, causing the host cell death before significant amounts of toxin can be harvested. Since clinical trials and commercial production require relatively large amounts of DT$_{ct}$GMCSF to be produced, a more efficient system for large scale production of DT$_{ct}$GMCSF is needed.

SUMMARY OF THE INVENTION

It has now been discovered that large amounts of biologically active DT$_{ct}$GMCSF can be produced using insect cell hosts. The fusion toxin produced in the insect cells is soluble, and can be easily purified to homogeneity by column chromatography. Surprisingly, DT$_{ct}$GMCSF was expressed in the cytoplasm of insect cells at a very high level. Approximately 8–10 mg/L of purified DT$_{ct}$GMCSF is routinely obtained from 1 liter of insect cell culture (about $10^9$ cells). Production of DT$_{ct}$GMCSF in insect cells thus provides a suitable means for generating sufficient amounts of DT$_{ct}$GMCSF for Phase I/II clinical trials and is amenable to further scale-up for commercial production.

The fusion protein is preferably expressed in an insect cell system using the baculovirus expression vector system. The fusion toxin can be isolated from the insect cells in high yield using a solubilization buffer that preferably includes a surfactant, for example Tergitol NP-40, followed by ion exchange chromatography. Preferably, a first column is neutral or slightly basic, at about pH 7.5 (preferably 7.4) and a second column is acidic at about pH 4–5 (preferably 4.1). This process results in simpler purification of high yield of biologically active fusion protein.

The invention also includes baculovirus expression vectors containing a nucleic acid sequence encoding the fusion toxin and insect cells useful to express large quantities of fusion toxin. Preferred expression vectors include a baculovirus expression system containing a DNA sequence encoding a DT$_{ct}$-targeting moiety fusion toxin. Insect cell cultures transformed or transfected with an expression vector provide for expression of fusion toxin, preferably in high yield.

BRIEF DESCRIPTION OF THE DRAWINGS

FIG. 3A is a graph showing fractions derived from the purification of BEV-derived DT$_{ct}$GMCSF through a RESOURCE Q column at pH 7.4.

FIG. 3B is a photograph showing a 10% SDS-PAGE gel identifying DT$_{ct}$GMCSF fractions.

FIG. 3C is a photograph showing Western blot analysis of selected DT$_{ct}$GMCSF fractions confirming the identity of a 61 kDa band as DT$_{ct}$GMCSF.

FIG. 5A is a photograph of a 10% SDS-PAGE gel showing purified $DT_{ct}$GMCSF. The arrow indicates the position of purified $DT_{ct}$GMCSF.

FIG. 5B is a photograph of a Western blot analysis showing a $DT_{ct}$GMCSF gel probed with anti-DT antibody.

FIG. 5C is a photograph of a Western blot analysis showing purified $DT_{ct}$GMCSF probed with anti-GMCSF antibody.

DETAILED DESCRIPTION OF THE INVENTION

Definitions

Figure 1:
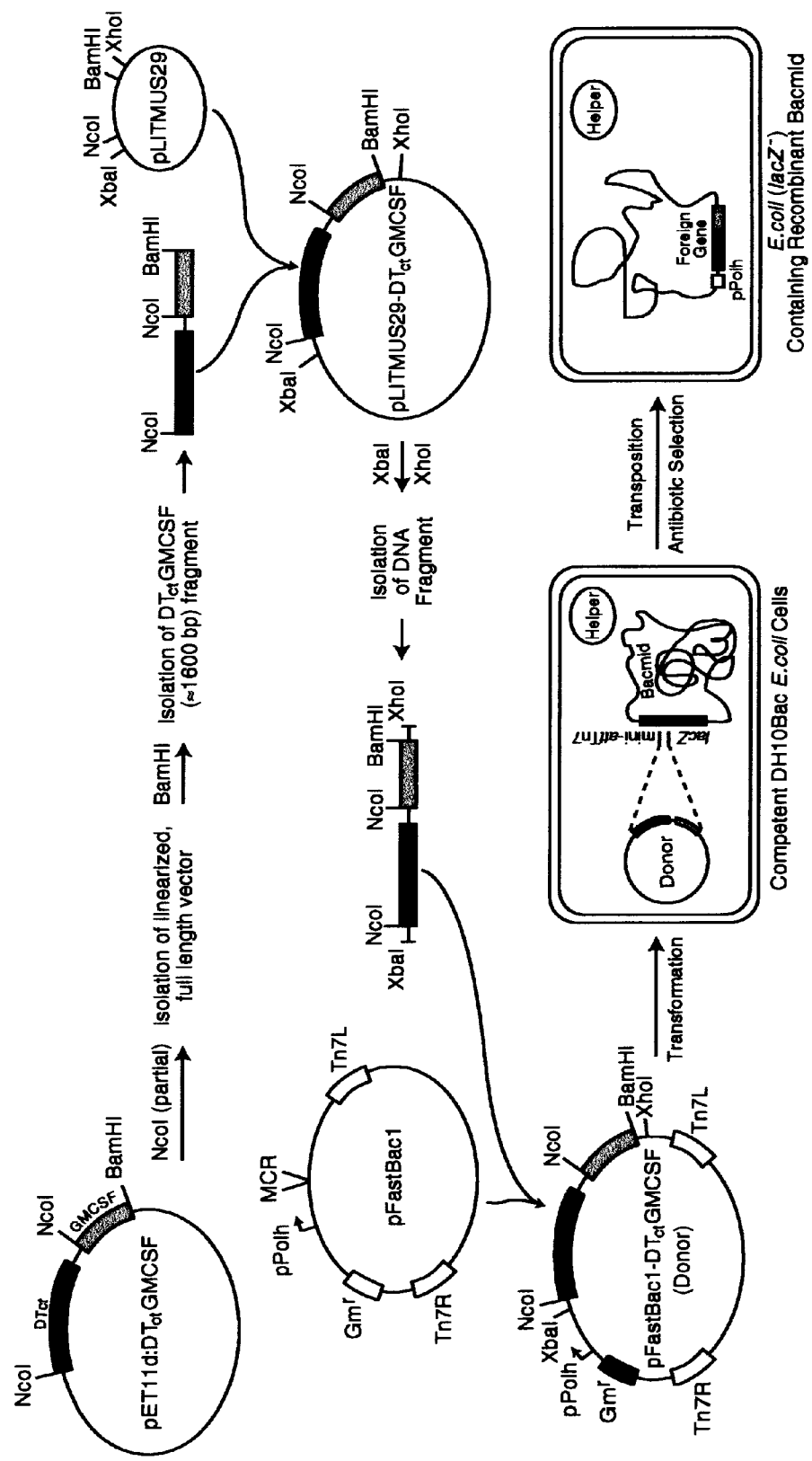
FIG. 1 is a schematic diagram showing the construction of a recombinant baculovirus carrying a DT$_{ct}$GMCSF fusion toxin.

Throughout the present application, the following terminology is used:

"fusion toxin" is meant to describe a toxin comprising at least two different proteins or portions thereof linked together. For purposes of this invention, the fusion toxin includes at least one toxin such as DT and at least one targeting moiety, for directing the toxin to a specific cell or tissue.

"DT" is meant to designate diphtheria toxin, a substance highly toxic to cells; the subscript "C" represents the catalytic ADP-ribosyltransferase domain; the subscript "T" represents the translocation segment which facilitates the transport of the toxin to the disease cell; hence, the term "$DT_{ct}$" represents a diphtheria toxin that preserves the portions of DT that include the lethal catalytic ADP-ribosyltransferase domain (c domain) and the contiguous portion of DT that is associated with translocation across cellular membranes (t domain).

"targeting moiety" is meant to designate any of a group of molecules, including proteins, which serve to direct or target the fusion toxin to a particular cell or tissue. Preferred targeting moieties for use in the invention include ligands such as cell surface receptors, especially those on tumor cells. Examples of targeting moieties include growth factors such as GMCSF (granulocyte-macrophage colony stimulating factor), EGF (epidermal growth factor), and MSH (melanocyte-stimulating hormone); cytokines, such as interleukins (IL-2, IL-4 and IL-6); and anti-cell surface receptor antibodies, such as those produced against specific tumor cell surface receptor antigens.

"cell surface receptor" is meant to designate a receptor located on the surface of a cell to which a targeting moiety will bind, and includes, for example, growth factor receptors such as EGF-R, GMCSF-R, or tumor cell specific antigen;

"expressing" or "expression" is meant to designate production of the protein fusion toxin from a nucleic acid sequence encoding the protein in a cellular host.

"isolating" or "isolation" is meant to designate the purifying of a compound from a mixture or a culture. Several means may be employed to isolate a fusion toxin, including ion exchange column chromatography, high pressure liquid chromatography, (HPLC) affinity chromatography, gel filtration, and the like.

"insect cell" is meant to designate a cell obtained from any insect of the order Lepidoptera (i.e., moths and butterflies) which is susceptible to infection by baculoviruses including but not limited to: *Spodoptera fruglperda* (IPLB-SF-21 or IPLB-SF-9), (fall army worm), *Trichoplusia ni* (BTI Tn5B1–4) (cabbage looper).

"BEV" or "BEVS" is an abbreviation for a baculovirus expression vector or baculovirus expression vector system. The baculovirus expression vector can be modified to include a DNA sequence encoding a fusion toxin. The baculovirus expression vector then provides for expression of the DNA sequence in a host cell.

The invention provides a method and compositions for large scale production of a fusion toxin comprising portions of diphtheria toxin fused to a targeting moiety. The targeting moiety is preferably a moiety that binds the fusion toxin to the desired cells. For example, tumor cells expressing a receptor for the targeting moiety. The invention provides for expression of the fusion toxin in insect cells using a baculovirus expression system. The fusion toxin is isolated from the insect cells in high yield, for example, using solubilization buffer with a surfactant and ion exchange chromatography, preferably including at least one column at acidic pH (3.5–4.5). The fusion toxin isolated according to a method of the invention is biologically active. The fusion toxin can be obtained in high yields, for example, about 10 mg/L, which is an 80 to 100 fold increase over the yield from *E. coli*.

Fusion Toxin

The fusion toxin of the present invention is a toxin or a portion of a toxin fused to a targeting moiety. The toxin is a protein selected to kill or inhibit the growth of selected cells, for example tumor cells. The targeting moiety is a protein selected to selectively transport the toxin to the surface of the selected cell or tissue.

Toxin

The toxin of the present invention is diphtheria toxin, commonly referred to as "DT". DT, a single polypeptide having a molecular weight of about 62,000, is highly toxic to cells. "$DT_{ct}$" is a segment of the whole DT protein. It is generally preferred not to utilize the entire diphtheria toxin protein due to its large size and potential for adverse side effects. "$DT_{ct}$" is a diphtheria toxin that preserves the portions of DT that include the lethal catalytic ADP-ribosyltransferase domain (c domain) and the contiguous portion of DT that is associated with translocation across cellular membranes (t domain).

Targeting Moiety

The targeting moiety of the fusion toxin is selected to bind the fusion toxin to a desired cell or tissue. For example, the targeting moiety can be selected for attachment to a specific surface receptor, such as a receptor which is expressed on the surface of the cell being targeted. In a preferred embodiment, the targeting moiety is a ligand which binds a receptor which is overexpressed on a tumor cell, thereby targeting the fusion toxin to the tumor cells. Examples of cell surface receptors (R) (and their corresponding targeting moieties) known to be found on tumor cells include GMCSF-R, IL-2-R, IL-4-R, IL-6-R, EGF-R, MSH-R, and other specific cell surface antigens. Once the targeting moiety binds the fusion toxin to the cell, the toxin can inhibit growth or induce cell death.

Production of DT fusion toxin, in particular $DT_{ct}GMCSF$, has been accomplished in *E. coli* host cells. $DT_{ct}GMCSF$ is a 521-amino acid residue chimeric protein containing a predicted amino-terminal methionine reside, followed by amino acid residues 1–385 of DT, a Ser-(Gly)$_4$-Ser-Met linker peptide, and mature human GMCSF. $DT_{ct}GMCSF$ is produced in *E. coli* only in limited amounts, typically about 100 micrograms/L. Surprisingly, in the method of the present invention, $DT_{ct}GMCSF$ is produced in much greater quantities, about 10 mg/L.

DNA sequences encoding diphtheria toxin and portions thereof have been described in Bendel, et al. 1997 Leuk. Lymphoma. 25, 257–270.

A preferred targeting moiety for the method of the present invention is granulocyte macrophage colony stimulating factor (GMCSF). The receptor for GMCSF is overexpressed on some tumor cells, including acute myeloid leukemia cells, and prostrate tumor cells. DNA encoding GMCSF can be produced synthetically using the method described in Bendel, et al., Supra.

Sequence Variations

Variations and modifications to the amino acid sequence of $DT_{ct}GMCSF$ can be made while still retaining functional activity, particularly the functional activity of binding to cells having a high level of GMCSF receptor expression. DNA encoding these variations including, for example, deletion, substitution or insertion mutants retaining a GMCSF receptor binding domain can be prepared synthetically or by modification of the DNA encoding GMCSF using restriction endonucleases or other standard methods. DNA encoding other targeting moieties is also available, for example, based on the known nucleic acid or amino acid sequence of the molecule.

Synthesis of the Fusion Toxin

A nucleic acid sequence encoding $DT_{ct}$ and a nucleic acid sequence encoding a targeting moiety are fused together using standard methods such as the recombinant methodology described in Bendel, et al. Supra. Optionally, a linking DNA sequence can be employed, such as that encoding a flexible peptide linker to bridge the toxin and targeting moiety sequences and/or provide for restriction endonuclease cleavage sites.

The fusion of a DNA sequence encoding $DT_{ct}$ and a sequence encoding a targeting moiety (such as GMCSF) forms a $DT_{ct}GMCSF$ fusion construct. The $DT_{ct}GMCSF$ fusion construct can then be modified, for example, by the addition of transcriptional and translation control elements that provide for expression of the construct in a desired host cell.

Expression Vectors

The fusion construct is preferably incorporated into an expression vector which facilitates production of the fusion toxin in a desired host cell. In the present invention, the desired host cell is an insect cell. Production of the fusion toxin in insect cells is facilitated, for example, by use of a recombinant baculovirus containing DNA sequences encoding the fusion toxin.

A DNA molecule encoding the recombinant $DT_{ct}GMCSF$ is inserted into an expression vector. The expression vector employed varies depending on the host cell to be transfected with the expression vector. That is, vectors are employed with transcription, translation and/or post-translational signals necessary for efficient expression of the DNA molecule in the various host cells into which the vectors are introduced. Such vectors are constructed and transfected into host cells by methods well known in the art. See Sambrook et al., *Molecular Cloning: A Laboratory Manual*, Cold Spring Harbor (1989) and O'Reilly et al., *Baculovirus Expression Vectors: A Laboratory Manual*, Freeman, N.Y. (1992). Preferred host cells for the $DT_{ct}GMCSF$ expression vectors include insect cells. Preferred insect cells include any insect of the order Lepidoptera (i.e., moths and butterflies) which is susceptible to infection by baculoviruses including but not limited to: *Spodoptera frugiperda* (fall army worm) cells such as Sf21 and Sf9 cells, and *Trichoplusia ni* (cabbage looper) cells such as BTI TRn5B1-4.

For production in insect cells, a nucleic acid sequence encoding the fusion toxin, for example $DT_{ct}GMCSF$, is transferred into an expression vector adapted for a particular host cell. Optionally, the nucleic acid sequence encoding the fusion toxin, the fusion construct, is first amplified and selected using a transfer vector. The transfer vector also provides for transfer into the expression vector. Transfer vectors include plasmids or bacmids and optionally have selectable markers that allow for identification of transformed and amplified cells. Selectable markers include antibiotic resistant markers and enzymatic markers.

Preferred transfer vectors include pET11d, pLITMUS-29, and pFastBac1. The transfer vector preferably includes a DNA sequence shared with an expression vector that can provide for recombination of the desired DNA sequence encoding the fusion toxin into the expression vector. This DNA sequence providing for recombination with the expression vector is preferably all or part of a transposable element. Transposable elements include Tn3, Tn5 and Tn7 elements. The preferred transposable element is the mini-transposon Tn7 element.

Expression vectors are adapted to provide for expression of the fusion toxin in a suitable host cell. Suitable host cells are insect cells, preferably from the fall army worm, ring worm, cabbage looper, and the like. Expression vectors may also include a selectable marker for identifying transformed cells. Transformed cells can also be detected by morphological changes. Selectable markers include antibiotic resistance genes. The preferred expression vector is one that can provide for a high yield of fusion toxin in insect cells, such as a baculovirus expression vector system (BEVS).

Transforming Host Cells

The expression vector encoding the fusion toxin is introduced into a suitable host cell by standard means. For example, the recombinant baculovirus can gain entry into insect cells through incubation of the cells with viral particles at a multiplicity of infection of about 0.01–100. Cells can be examined for the presence of infection by morphological changes, including the formation of plaques. Plaques are selected and are then cultured to provide for high yield of expression of the fusion toxin.

Baculovirus Carrying DT$_{ct}$GMCSF

FIG. 1 shows a schematic diagram of the construction of a recombinant aculovirus or bacmid carrying a nucleic acid sequence encoding DT$_{ct}$GMCSF fusion oxin. The intact DT$_{ct}$GMCSF fusion construct is excised from the pET11d-DT$_{ct}$GMCSF expression vector by a two step digestion. First, an NcoI partial digestion is carried out, followed by purification of linearized full length vector. The NcoI linearized vector is then completely digested with BamHI and the 1.6 kb DT$_{ct}$GMCS fragment is released and purified. This NcoI-BamHI 1.6 kb fragment is then ligated into similarly digested pLITMUS-29. The resulting vector, pLITMUS-29-DT$_{ct}$GMCSF, is then digested with XbaI and XhoI to provide the XbaI-XhoI DT$_{ct}$GMCSF fragment which is then further ligated into similarly digested pFastBac1, resulting in pFastBac1-DT$_{ct}$GMCSF.

The recombinant bacmid is generated in DH10Bac cells when the mini-Tn7 element from pFastBac1-DT$_{ct}$GMCSF (containing DT$_{ct}$GMCSF and a gentamicin resistance marker) transposes to the mini-attTn7 attachment site on the bacmid. This transposition event results in the disruption of expression of the lacZα peptide, which allows for the identification of colonies containing recombinant bacmid as white in a background of blue colonies containing unaltered bacmid when plated in the presence of Bluo-gal (Gibco-BRL). White colonies are then picked and amplified, and bacmid DNA is purified.

The recombinant bacmid DNA is generated in *E. coli* by the Bac-to-Bac system developed by Luckow et al., *J. Virol* 67:4566 (1993). The recombinant baculovirus particles then carry the DNA sequence encoding the fusion toxin and can be utilized to infect a suitable host cell such as Sf21, Sf9, or BTI Tn5B1-4 insect cells.

Culturing Insect Cells

The purified recombinant bacmid is used to transfect suitable host insect cells. The insect cells are selected for their resistivity to diphtheria toxin. Suitable insect cells can be commercially obtained, for example, from Invitrogen Corp. (Carlsbad, Calif.).

In a preferred method, the bacmid carrying the fusion toxin is transfected into the host cells by addition of an amount of purified bacmid to a culture of the host cells using transfection methods such as liposome mediated transfection as described by O'Reilly et al., *Baculovirus expression vectors, A Laboratory Manual* (1992).

The infected culture is then allowed to grow until a desired yield of the fusion toxin is expressed in the cells. The cells are preferably grown at 26–28° C. for about 48 hours. The cells are then examined for altered cellular growth and morphology. Cells from infected cultures are screened for the presence of the 61 kDa fusion toxin using SDS-PAGE and/or Western blots. The expression vector is passaged in the cells a limited number of times, generally no more than 4 times to limit the formation of defective interfering particles.

Isolation and Purification of Fusion Toxin

Once expressed in the cells, the fusion toxin is isolated, purified and characterized for biological activity.

The fusion toxin can be isolated from the cell culture supernatant or cells depending on whether the fusion toxin is secreted. In the baculovirus infected insect cells, it was found that a high level of fusion toxin was produced in the cytoplasm of the insect cells. The expression of the fusion toxin in this system resulted in a yield of about 8 to 10 mg/L of purified DT$_{ct}$GMCSF. This is in contrast to other cell culture systems such as *E. coli*, whose yield of fusion toxin is only about 100 micrograms/L.

The method of the invention also provides for isolation and purification of the fusion toxin under less harsh conditions resulting in a higher yield of biologically active material. The fusion toxin is isolated from cells, for example, by incubating the cells in a cell lysis buffer. The cell lysis buffer preferably includes a surfactant such as Tergitol NP-40™ at a concentration of about 1%, which readily solubilizes the fusion toxin. It has been shown that other detergents such as CHAPS™, Tween 20™ and Triton X400™ were not as effective in solubilizing the fusion toxin from the cell lysate.

Once solubilized from the cells, the fusion toxin can be further isolated and purified using column chromatography. The fusion toxin can be separated from other soluble proteins using ion exchange chromatography, hydrophobic interaction chromatography, and/or size exclusion chromatography.

It is preferred that at least one step of the purification includes ion exchange chromatography at acidic pH since the theoretical pI of the fusion toxin is acidic. It is believed that the pI of the DT$_{ct}$GMCSF is less than pH 3.5 and that yield of the fusion toxin can be enhanced by conducting ion exchange chromatography more preferably at a pH of 3.5 to 4.5.

Chromatography fractions containing the fusion toxin can be detected, for example by Western blot or other immunoassay, using antibodies recognizing either the toxin, the targeting moiety, or both. Fractions which contain the fusion toxin are pooled and then subjected to further column chromatograph, if necessary, to obtain a purity of about 75 to 100%, preferably about 90 to 100%. The purified toxin is then characterized for biological activity. Optionally, the purified toxin may be filtered using disposable sterile filters to obtain a sterile injectable solution.

Figure 2:
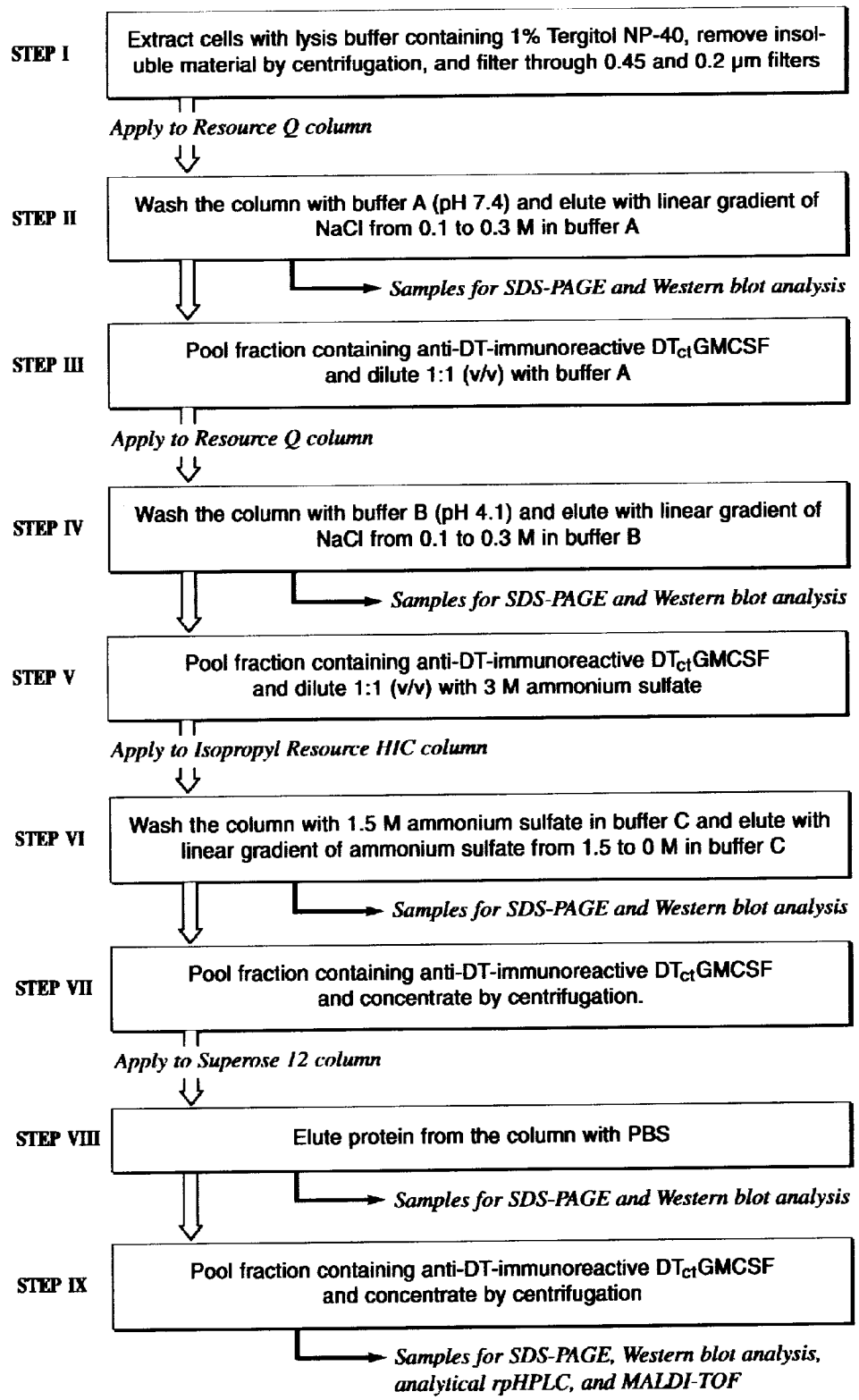
FIG. 2 is a flow chart showing a scheme for the purification of fusion toxin.

FIG. 2 is a flow chart depicting one method for extracting, purifying and concentrating a fusion toxin, for example, DT$_{ct}$GMCSF, from transfected host insect cells. DT$_{ct}$GMCSF was solubilized using a cell lysis buffer including Tergitol NP-40 at about 1%. The cell lysate was centrifuged and the fusion toxin was further isolated and purified using column chromatography.

Columns useful for the purification of DT$_{ct}$GMCSF produced by the method of the present invention include, for example, RESOURCE Q column at pH 7.4. Typical results using this column are shown in FIG. 3. The DT$_{ct}$GMCSF can then be purified at acidic pH, for example, through a RESOURCE Q column at pH 4.1, followed by an isopropyl RESOURCE HIC column and size exclusion chromatography. Fractions containing DT$_{ct}$GMCSF are characterized, for example, by Western blot analysis using antibodies against the DT toxin. As shown in the example below, toxin of about 95% purity, as determined by analytical reverse phase HPLC, can be obtained at a yield of about 8–10 mg/L.

Characterization of Fusion Toxin

The isolated and purified fusion toxin is characterized for biological activities, including cytotoxicity and binding to selected cells.

Several methods to measure cytotoxicity of the fusion toxins are known, as described in Perentesis et al., *Clinical Tumor Research* 3:347 (1997). These methods include measuring inhibition of protein synthesis with labeled amino acids, such as tritiated leucine, measuring cell lysis, measuring apoptosis and measuring inhibition of cell growth.

A preferred method for analyzing cell cytotoxicity is to detect apoptosis of the cells after exposure to the fusion toxin. Apoptosis is identified by distinct ultrastructural features and a ladder like DNA fragmentation pattern that results from endonuclease-mediated cleavage of DNA into an oligonucleosome length fragments.

Alternatively, labeled cells or cell lines can be examined for the release of the label upon cell death after exposure to the fusion toxin in standard assays. Examples of such labels include $51_{cr}$ and other radioactive labels, and flourscein, MTT and other dyes.

The cells or cell lines used to assay biological activity are preferably tumor cells. Tumor cells can be derived from a cell line or from human tissue samples. The type of cells useful in the assay are based on the selection of the targeting moiety. For example, GMCSF targets acute hematopoietic tumor cells such as acute myelogenous leukemia cells and/or prostate tumor cells. The interleukin molecules target other types of leukemia cells. Epidermal growth factor targets breast tumor cells. These cells are useful for analysis of fusion toxin cytotoxicity for fusion toxins having the appropriate targeting moiety.

Fusion toxin preparations that have at least about 8 to 10 mg/L of biologically active protein are desired to provide sufficient material for clinical and/or preclinical treatment of tumor cells. Preferably, these toxin preparations are free of contaminants that cause undesirable side effects such as endotoxin. Purity levels of about 75 to 100%, preferably 90 to 100% are acceptable for human treatment.

In a preferred embodiment of the invention, $DT_{ct}GMCSF$ is inserted into an baculovirus expression vector and expressed in insect cells. The expressed protein is useful in inhibiting the growth of or inducing cell death of tumor cells.

EXAMPLES

The invention may be better understood by reference to the following Examples, which are not intended to limit the invention in any way.

Example 1

Production of $DT_{ct}GMCSF$ Fusion Toxin

A detailed method for producing $DT_{ct}GMCSF$ fusion toxin according to the present method is described below.

$DT_{ct}GMCSF$ fusion construct was prepared as described in Bendel, et al. *Leuk Lymphoma.* 25, 257–270 (1997). Intact $DT_{ct}GMCSF$ fusion toxin construct was excised from the pET11d-$DT_{ct}GMCSF$ expression vector by a two step digestion protocol. The process is schematically depicted in FIG. 1.

First, an NcoI partial digestion was carried out followed by purification of linearized (once-cut) pET11d-$DT_{ct}GMCSF$ by the method of Langridge et al. (Langridge, J., Langridge, P., and Bergquist, P. L., *Anal Biochem.* 103:264–271 (1980)). The NcoI linearized vector was completely digested with BamHI and the 1.6 kb fragment corresponding to the entire $DT_{ct}GMCSF$ construct was purified, again by the method of Langridge et al. The NcoI-BamHI fragment was then ligated into similarly digested pLITMUS-29 (New England Biolabs, Inc., Beverly, Mass.). The resulting vector, pLITMUS-29-$DT_{ct}GMCSF$, allowed the removal of the entire $DT_{ct}G$-MCSF fusion gene as an XbaI-XhoI fragment. This XbaI-XhoI $DT_{ct}GMCSF$ fragment was finally ligated into similarly digested pFastBac1 (Gibco-BRL, Grand Island, N.Y.) resulting in pFastBac1-$DT_{ct}GMCSF$, the transfer vector used in the construction of recombinant baculovirus carrying the intact $DT_{ct}GMCSF$ fusion gene construct.

Recombinant baculovirus carrying the $DT_{ct}GMCSF$ fusion toxin gene was generated using the Bac-to-Bac system (Gibco-BRL, Grand Island, N.Y.) developed by Luckow et al. which is based on generation of recombinant virus by site-specific transposition in *Escherichia coli.* (Luckow, et al. *J Virol.* 67:4566–4579 (1993)). Briefly, the transfer vector, pFastBac1-$DT_{ct}GMCSF$, was used to transform DH10Bac *E. coli* cells which carry a baculovirus chromosome as a shuttle vector (bacmid) containing the low-copy-number mini-F replicon, a kanamycin resistance marker, and a segment of DNA encoding the lacZα peptide. The recombinant bacmid was generated when the mini-Tn7 element from pFastBac1-$DT_{ct}GMCSF$ (containing $DT_{ct}G$-MCSF and a gentamicin resistance marker) transposed to the mini-attTn7 attachment site on the bacmid. Transposition functions were provided in trans by a helper plasmid (pMON7124) in DH10Bac. This transposition event resulted in the disruption of expression of the lacZα peptide which allowed for the identification of colonies containing recombinant bacmid as white in a background of blue colonies containing unaltered bacmid when plated in the presence of Bluo-gal™ (Gibco-BRL). After 36–48 hours, white colonies were picked and restreaked on Bluo-gal plates to confirm the disruption of the lacZα peptide. Two ml cultures were then grown in LB medium and the bacmid DNA was purified according to the manufacturer's instructions.

Host Cells

Sf21 (IPLB-SF21-AE) cells, derived from the ovarian tissue of the fall armyworm *Spodoptera frugiperda,* were obtained from Invitrogen Corp. (Carlsbad, Calif.) and maintained at 26–28° C. in Grace's insect cell medium (Gibco-BRL) supplemented with 10% FBS and 1.0% antibiotic/antimycotic (Gibco-BRL). Stock cultures were maintained in suspension at $0.2–1.6 \times 10^6$/ml in a total culture volume of 600 ml in 1 liter spinner flasks (from Bellco Glass Inc., Vineland, N.J.) at 80–100 rpm. Cell viability was maintained at 95–100% as determined by trypan blue dye exclusion. The GMCSF-R bearing human leukemia cell line, HL-60, was obtained from American Type Culture Collection (Rockville, Md.).

Transfecting Host Cells with $DT_{ct}GMCSF$

Purified bacmid DNA, produced above, was then used to transfect the Sf21 cells according to the liposome-mediated protocol (as taught by O'Reilly, D. R., Miller, L. K., and Luckow, V. A. (1992) "Baculovirus expression vectors: A laboratory manual," Freeman, N.Y.) with the Cellfectin reagent (Gibco-BRL). After 4–6 days of incubation at 28° C. the transfected cells were visually examined to confirm morphological changes associated with baculoviral infection. Viral particles were purified using the plaque purification method described in O'Reilly et al. as above. Several well separated, individual plaques were identified visually and propagated in monolayer cultures of Sf21 cells. Infected cultures were initially identified by altered cellular growth and morphology under microscopic examination. Cells from these positive cultures were then screened for the presence of a unique 61 kDa protein by sodium dodecyl sulfate polyacrylamide gel electrophoresis (SDS-PAGE) and simple Commassie blue staining.

Example 2

Large Scale Expression of $DT_{ct}GMCSF$

Large scale experiments were conducted by infecting one liter cultures of Sf21 cells in 3 L Bellco spinner flasks ($1.0–1.2 \times 10^6$ cells/ml) during logarithmic growth with 25 ml of the bacmid viral stock solution (approx. $2.5 \times 10^8$ pfu/ml). This infection protocol resulted in a multiplicity of infection of approximately 6 pfu/cell. The viral stock solutions were passaged no more than 3 times following plaque purification prior to use in these large scale infections in order to minimize the presence of defective interfering particles. These cultures were incubated at 28° C. and stirred at 80–100 rpm using a magnetic stirrer (Bellco Glass Inc., Vineland, N.J.) for 48 hours. Infected cells were harvested by gentle centrifugation in a Beckman GS-6 centrifuge at 500×g for 7 minutes at room temperature. Cells from 1 L cultures were divided into two aliquots (approximately 4 g of wet cell paste) and immediately flash-frozen at −80° C. and then stored at −80° C. until purification of $DT_{ct}GMCSF$.

Example 3

Purification of $DT_{ct}GMCSF$

Purification of the $DT_{ct}GMCSF$ fusion toxin from insect cell culture was a simple procedure under less harsh conditions that gave a high yield (approximately 100 times greater) of biologically active material as compared with *E. coli* based systems. Solubilization of the fusion protein from insect cells was trivial compared with *E. coli.* A schematic diagram showing the purification scheme is shown in FIG. 2.

For $DT_{ct}$GMCSF purification, the infected frozen Sf21 cells (approximately 4 g cell paste) were lysed by incubation for 1 hour with gentle agitation at 4° C. in 10 ml of extraction buffer (50 mM Tris-HCl, pH 7.4, 1 mM EDTA, and 1 mM DTT) containing 1% Tergitol NP-40 and Complete™ protease inhibitors (Boeringer Mannheim). All subsequent steps were performed at 4° C. unless otherwise noted. Following removal of insoluble material by centrifugation at 35,000×g for 20 minutes in a Beckman Optima LE-80 K ultracentrifuge, the supernatant was filtered through tandem 0.45 $\mu$m and 0.2 $\mu$m syringe filters and was immediately subjected to chromatography to minimize degradation and possible loss of activity.

A fast protein liquid chromatography system from Pharmacia Biotech Inc. (Piscataway, N.J.) was used in the purification procedures. The protein concentration was determined by absorbance at 260 and 280 nm and by Bradford analysis (Bradford, M. M., *Anal Biochem.* 72, 248–254.). Filtered cell extract was loaded onto a 6 ml RESOURCE Q ion exchange column (Pharmnacia) pre-equilibrated with 20 mM sodium phosphate buffer, pH 7.4 (buffer A). After loading the sample, the column was washed with 15 ml of buffer A+0.1 M NaCl, and protein was eluted from the column with a 30 ml linear gradient from 0.1 to 0.3 M NaCl in buffer A, at a flow rate of 1 ml/minute and 1 ml fractions were collected. FIG. 3A shows the chromatogram of the elution of the 35,000×g supernatant from the RESOURCE Q column at pH 7.4. The darkened area shows the $DT_{ct}$GMCSF peak consisting of fractions 29–33. The salt gradient used in the elution from the column is shown as dashed line 32.

Eluted fractions containing $DT_{ct}$GMCSF fusion protein were identified by SDS-PAGE and Western blotting using anti-DT antiserum, pooled, and concentrated using an Amicon 30 centriprep concentrator. Samples of cell lysate or column fractions were resolved by SDS-PAGE on 10% polyacrylamide slab gels. Molecular weight standards of 14–97 kDa were obtained from Pharmacia and run in the lanes indicated. The proteins were fixed and stained with Coomassie Blue R-250, dried and transferred onto PVDF Immobilon P membranes (from Millipore) at 120 mA for 1 hour in a Hoefer TE70 series semi-dry transfer unit. Standards were visualized by Ponceau S (Sigma) and the membrane blocked for 1 hour with 3% BSA in 10 mM Tris-HCl, pH 7.4, 150 mM NaCl and 0.1% Tween 20 (TBST). The membranes were incubated with anti-DT antibody (Biogenesis, Inc., Sundown, N.H.) or anti-GMCSF antibody (Santa Cruz Biotechnology, Inc., Santa Cruz, Calif.) (1:3000 dilution in TBST) followed by secondary antibodies labeled with HRP (1:20,000 in TBST) and developed by enhanced chemoluminescence (ECL, Amersham).

FIG. 3B shows representative fractions from the peaks detected from the chromatogram fractionated through a 10% SDS PAGE gel to identify $DT_{ct}$GMCSF containing fractions. An intense protein band at approximately 61 kDa, corresponding to $DT_{ct}$GMCSF, can be seen in fractions 29–33. The left lane contains the material loaded onto the column. The arrow on the left indicates the position of $DT_{ct}$GMCSF. FIG. 3C shows the Western analysis of selected fractions to confirm the identity of the 61 kDa protein band as $DT_{ct}$GMCSF. The arrow on the right indicates the position of $DT_{ct}$GMCSF.

The concentrate from the RESOURCE Q column at pH 74 was immediately diluted 1:1 with buffer A and reloaded onto a 6 ml RESOURCE Q column equilibrated with 20 mM sodium phosphate, pH 4.1 (buffer B). The column was washed with 10 ml buffer B and bound protein was eluted with a 30 ml linear gradient from 0.1 to 0.3 M NaCl in buffer B. The flow rate was 1 ml/minute, and 1 ml fractions were collected.

Eluted fractions were again analyzed by SDS-PAGE and Western blotting. FIG. 4A shows polyacrylamide gel electrophoretic analysis of selected fractions eluted from the RESOURCE Q column at pH 4.1. Aliquots were run on a 10% SDS-PAGE gel and stained with Coomassie blue. Molecular weight standards were run on the same gel, as indicated in kDa. FIG. 4B shows Western blot analysis of fractions eluted from the RESOURCE Q column at pH 4.1. Aliquots were run on a 10% SDS-PAGE gel. After transferring to PVDF membrane and blocking with BSA, $DT_{ct}$-GMCSF was detected using anti-DT antibody as described above. The results show the presence of $DT_{ct}$GMSCF in fractions 25–30.

Fractions containing the anti-DT immunoreactive peak were pooled, mixed with an equal volume of 3 M $(NH_4)_2SO_4$ and loaded onto a 1 ml Isopropyl RESOURCE HIC column (Pharmacia) preequilibrated with 10 mM Tris-HCl, pH 7.2 (buffer C) containing 1.5 M $(NH4)_2SO_4$. The column was washed with 5 ml of buffer C containing 1.5 M $(NH_4)_2SO_4$ and protein was eluted with a linear gradient of $(NH_4)_2SO_4$ from 1.5 M to 0 M in buffer C. The flow rate was 1 ml/minute, and 1 ml fractions were collected. Eluted fractions were analyzed by SDS-PAGE. FIG. 4C shows polyacrylamide gel electrophoretic analysis of peak fractions eluted from the Isopropyl RESOURCE HIC column. Aliquots were run on a 10% SDS-PAGE gel and stained with Coomassie blue. Mr is given in kDa on the left. $DT_{ct}$GMCSF was detected in fractions 12–14.

Fractions containing $DT_{ct}$GMCSF were pooled and concentrated using an Amicon 30 centriprep concentrator. The concentrated fractions were applied to a Superose 12 10/30 size exclusion column (Pharmacia) preequilibrated with PBS, and protein was eluted with PBS at a flow rate of 0.5 ml/minute; 1 ml fractions were collected. Eluted $DT_{ct}$G-MCSF was stored at 4° C.

The purity of $DT_{ct}$GMCSF was evaluated and the results are shown in FIG. 5. For FIG. 5A, aliquots of purified DT$_{ct}$GMCSF as follows: lane 1, 0.5 mg; lane 2, 1.0 mg; lane 3, 1.5 mg; lane 4, 2.0 mg; lane 5, 2.5 mg; lane 6, 5.0 mg were run on a 10% SDS-PAGE gel and stained with Coomassie blue. Mr is given in kDa on the left; the arrow indicates the position of DT$_{ct}$GMCSF. FIG. 5B shows a Western blot analysis of the purified DT$_{ct}$GMCSF with anti-DT antibody.

Aliquots of purified DT$_{ct}$GMCSF (lane 1, 0.5 mg; lane 2, 1.0 mg; lane 3, 1.5 mg; lane 4, 2.0 mg; lane 5, 2.5 mg) were run on a 10% SDS-PAGE gel. After transferring to a PVDF membrane and blocking with BSA, DT$_{ct}$GMCSF was detected using anti-DT antibody as described previously. Mr is given in kDa on the left; the arrow indicates the position of DT$_{ct}$GMCSF. FIG. 5C also shows a Western blot analysis of the purified DT$_{ct}$GMCSF with anti-GMCSF antibody. Aliquots of purified DT$_{ct}$GMCSF (lane 1, 0.5 mg; lane 2, 1.0 mg; lane 3, 1.5 mg; lane 4, 2.0 mg; lane 5, 2.5 mg) were run on a 10% SDS-PAGE gel. After transferring to a PVDF membrane and blocking with BSA, DT$_{ct}$GMCSF was detected using anti-GMCSF antibody as described previously. The arrow indicates the position of DT$_{ct}$GMCSF.

Figure 5D:
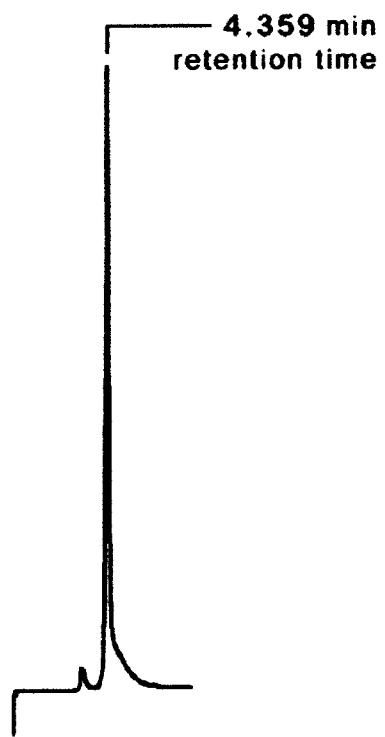
FIG. 5D is a graph showing results of HPLC analysis of purified $DT_{ct}$GMCSF.

FIG. 5D is a graphical depiction of the reverse phase HPLC of the purified DT$_{ct}$GMCSF. The HPLC instrument used for the test was a Hewlett Packard 1100 Series HPLC liquid chromatography system coupled to a HP 3396 Series III integrator. The column was a Microsorb-MV C8, 250× 4.6 mm I.D., 5-μm particle size, 300-A pore size (Rainin). Conditions: linear 50%–90% A–>B gradient (4%/minute), where eluent A is water and eluent B was acetonitrile, both eluents contained 0.1% TFA; flow-rate 1 ml/minute; detection at 280 nm. These results indicate the DT$_{ct}$GMCSF toxin preparation is approximately 95% pure.

Figure 5E:
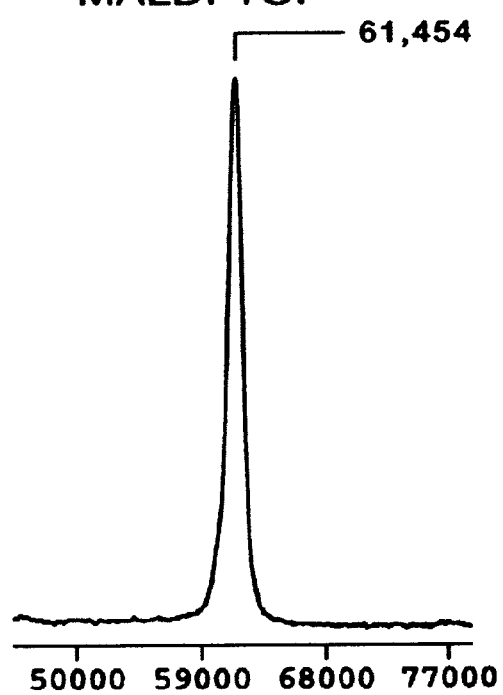
FIG. 5E is a graph showing the high-mass portion of the mass spectrum analysis of purified $DT_{ct}$GMCSF.

FIG. 5E shows the high-mass portion of the MALDI mass spectrum of the purified DT$_{ct}$GMCSF. DT$_{ct}$GMCSF was analyzed by matrix-assisted laser desorption/ionization time of flight (MALDI-TOF) mass spectrometry (Hewlett-Packard). In conjunction with the instrument were a sample preparation assembly model G2024A including a high vacuum pump and a Dos-Chem station controller model G1030A. Before starting the experiment, the instrument was calibrated with protein standards G2025A supplied by Hewlett Packard. 10 μl of a sample of DT$_{ct}$GMCSF in phosphate buffer was mixed with 10 ml of Matrix substance sinapinic acid. One microliter of this mixture was applied on the gold surface and subsequently evaporated under vacuum to establish a uniform coating. The sample was then placed in the instrument and the laser beam was applied on the sample both in single shot as well as multiple shot modes to observe the peaks corresponding to the molecular ions. Ionization was accomplished with N$_2$ laser radiating at a wavelength of 337 nm (5 ns pulses, laser energy: 1.97 mJ). The analyzer was used in the linear mode at an accelerating voltage of 28 kV. The spectra obtained represent the sum of consecutive laser shots and have not been smoothed.

In order to maximize the recovery of DT$_{ct}$GMCSF, the inclusion of Tergitol NP-40 (surfactant from Union Carbide) in the lysis buffer to a final concentration of 1% rendered the fusion toxin completely soluble. DT$_{ct}$GMCSF containing Sf21 cells were lysed in lysis buffer+1% Tergitol NP-40, and the soluble fraction containing DT$_{ct}$GMCSF was applied to a RESOURCE Q column. The DT$_{ct}$GMCSF quantitatively bound to the RESOURCE Q column at pH 7.4. Both anti-DT and anti-GMCSF antibodies recognized the same size protein band on Western blot analyses (data not shown) and therefore, in all further experiments only anti-DT antibodies were used. IEF analysis of partially purified DT$_{ct}$GMCSF revealed that the fusion toxin had a particularly low pI of <3.5 which suggested that additional purification could be achieved by utilizing the RESOURCE Q column at a lower pH (data not shown). Accordingly, the eluate from the RESOURCE Q column at pH 7.4 was diluted 1:1 in buffer A (pH 7.4) to reduce the salt concentration and reapplied to the column. The column was then washed with buffer B, (pH 4.1), and the fusion toxin was again eluted from the column with a linear gradient from 0 to 300 mM NaCl in buffer B, (pH 4.1; FIG. 3). Remaining minor contaminants were removed by the use of two additional columns; employing hydrophobic interaction and size exclusion chromatography.

Figure 4A:
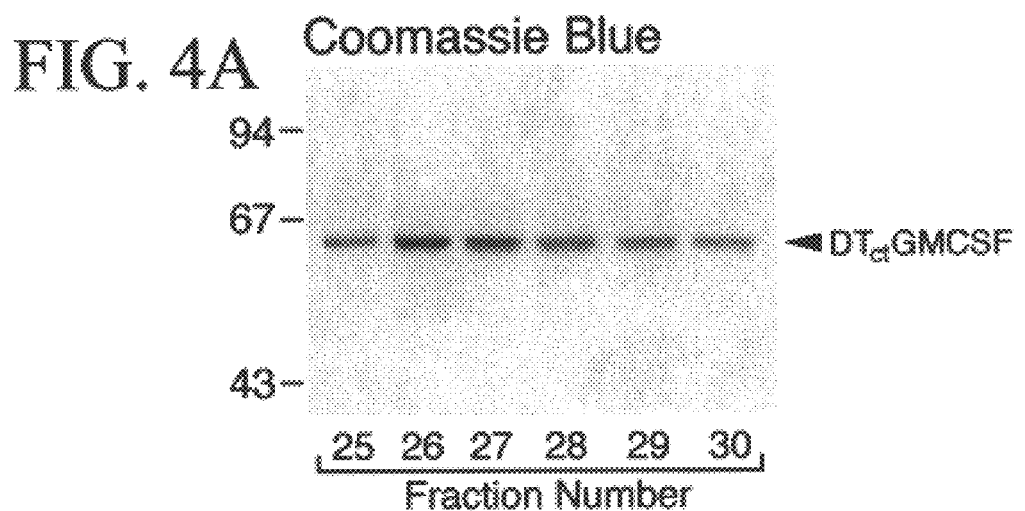
FIG. 4A is a photograph showing a 10% SDS-PAGE gel of fractions from purification of $DT_{ct}$GMCSF through a RESOURCE Q column at pH 4.1.
Figure 4B:
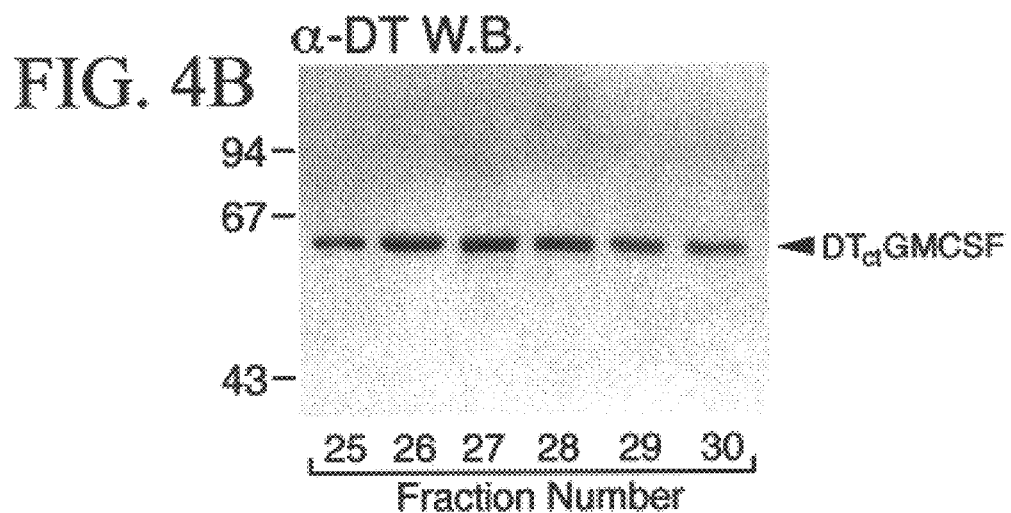
FIG. 4B is a photograph showing Western blot analysis of fractions from the RESOURCE Q column.
Figure 4C:
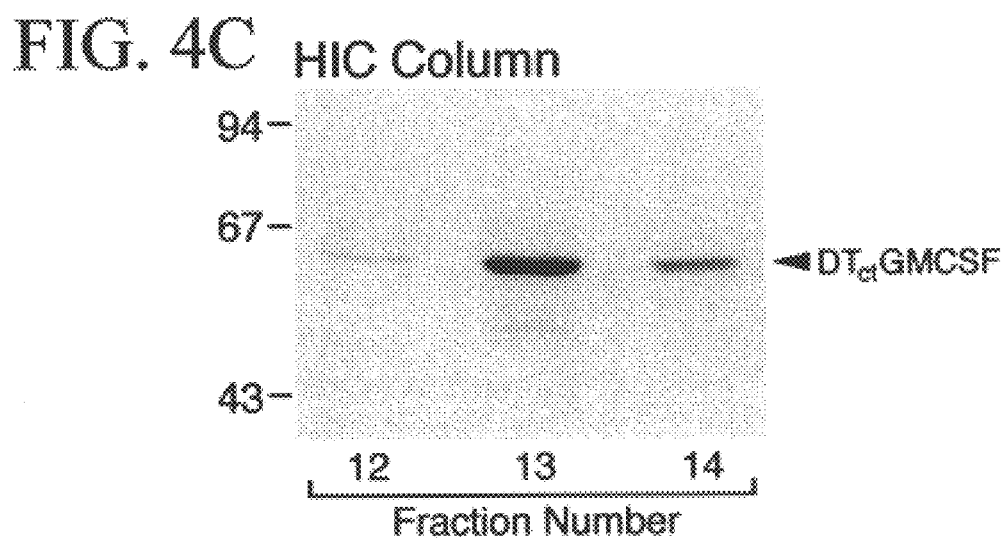
FIG. 4C is a photograph of a 10% SDS-PAGE analysis of peak fractions of $DT_{ct}$GMCSF from an Isopropyl RESOURCE HIC column.

Table 1 summarizes the results of the purification of DT$_{ct}$GMCSF. The final purification step of DT$_{ct}$GMCSF yielded only one major protein band of approximately 61 kDa and 95% purity as determined by analytical reverse phase HPLC. The pI of the purified DT$_{ct}$GMCSF was determined to be <3.5 (data not shown). The MOLDI-TOF analysis of DT$_{ct}$GMCSF yielded a single peak with an estimated molecular mass value of 61,454 (FIG. 4).

TABLE 1

Purification of DT$_{ct}$GMCSF from 1L culture

| Purification Step | Total protein, mg | DT$_{ct}$GMCSF, mg | Fold Purification, DT$_{ct}$GMCSF content (%) | Yield, % |
|---|---|---|---|---|
| Tergitol NP-40 extract | 69.0 | 10.8 | 1.0 (15.6) | 100 |
| Resource Q, pH 7.4, column | 11.4 | 10.2 | 5.7 (89) | 94 |
| Resource Q, pH 4.1, column | 10.5 | 9.6 | 5.9 (91) | 89 |
| HIC column | 9.3 | 8.7 | 6.0 (93) | 81 |
| Superose 12 10/30 column | 8.4 | 8.1 | 6.2 (96) | 75 |

Example 4 —Biological Activity of BEV Derived DT$_{ct}$GMCSF

Biological activity of the purified fusion toxin was assayed in HL-60 myeloid leukemia cells by incubating the cells with varying amounts of DT$_{ct}$GMCSF for 36 hours. Following this incubation period, DNA from supernatants of Triton X-100 lysates was prepared as described in Uckun et al., *Science* 267:886 (1995). DNA was fractionated by electrophoresis through 1% agarose gels. Fractionated DNA was visualized by UV light after being stained with ethidium bromide.

In parallel, HL-60 cells were analyzed for apoptotic changes by quantitative DNA flow cytometry, as previously described by Myers, et al., *Proc Natl Acad Sci USA*. 92:9575–9579 (1995). The demonstration of apoptosis was also performed by the in situ nick-end-labeling method using the ApopTag in situ detection kit (Oncor, Gaithersburg, Md.) according to the manufacturer's recommendations. Exponentially growing cells were seeded in 6-well tissue culture plates at a density of $5 \times 10^5$ cells/well and cultured for 36 hours at 37° C. in a humidified 5% CO$_2$ atmosphere. The culture medium was carefully aspirated and replaced with fresh medium containing DT$_{ct}$GMCSF at the indicated concentrations. After 36 hours of incubation at 37° C. in a humidified 5% CO$_2$ incubator, the supernatants were carefully aspirated and the cells were collected in a 15 ml centrifuge tube, washed with medium, and collected by centrifugation at 1000 rpm for 5 minutes. The cell pellets were resuspended in 50 ml of PBS, transferred to poly-L-lysine coated coverslips and allowed to adhere for 15 minutes. The cells were washed once with PBS and subsequently incubated for 1 hour at 37° C. with the reaction mixture containing terminal deoxynucleotidyl transferase (TdT) and digoxigenin-11-UTP for labeling of the exposed 3'-hydroxyl termini of fragmented nuclear DNA. The cells were again washed with PBS and incubated with anti-digoxigenin antibody conjugated to FITC for 1 hour at room temperature to detect the incorporated dUTP. After washing the cells with PBS, the coverslips were mounted onto slides with Vectashield containing propidium iodide (Vector Labs, Burlingame, Calif.) and viewed with a confocal microscope. Non-apoptotic cells (untreated control, shown in FIG. 7B) do not incorporate significant amounts of dUTP due to lack of exposed 3'-hydroxyl ends, and consequently have much less fluorescence than apoptotic cells ($DT_{ct}$GMCSF treated, shown in FIG. 7C) which have an abundance of exposed 3'-hydroxyl termini. In control reactions, the TdT enzyme was omitted from the reaction mixture.

Cytotoxicity Assays

The cytotoxic effect of $DT_{ct}$GMCSF on HL-60 cells was examined by means of a non-radioactive, colorimetric assay using 3-[4,5-dimethylthiazol-2-yl]-2,5-diphenyl tetrazolium bromide (MTT) (27; 28) (Boehringer Mannheim Corp., Indianapolis, Ind.) in which MTT is metabolized to formazan by viable cells. Assays were carried out in 96-well plates in which $2.5 \times 10^4$ cells were seeded per well and incubated for 36 hours at 37° C. prior to drug exposure. On the day of treatment, culture medium was carefully aspirated from the wells and replaced with fresh medium containing $DT_{ct}$GMCSF at eight different concentrations ranging from 3.9 nM to 500 nM. Triplicate wells were used for each concentration tested. The cells were incubated with $DT_{ct}$GMCSF for 36 hours at 37° C. in a humidified 5% $CO_2$ atmosphere. To each well, 10 μl of MTT (0.5 mg/ml final concentration) were added and the plates were incubated at 37° C. for 4 hours to allow MTT to be converted to formazan crystals by reacting with metabolically active cells. The formazan crystals were solubilized overnight at 37° C. in a solution containing 10% SDS in 0.01 M HCl. The absorbance of each well was measured in a microplate reader (Labsystems) at 540 nm and a reference wavelength of 690 nm.

Figure 6:
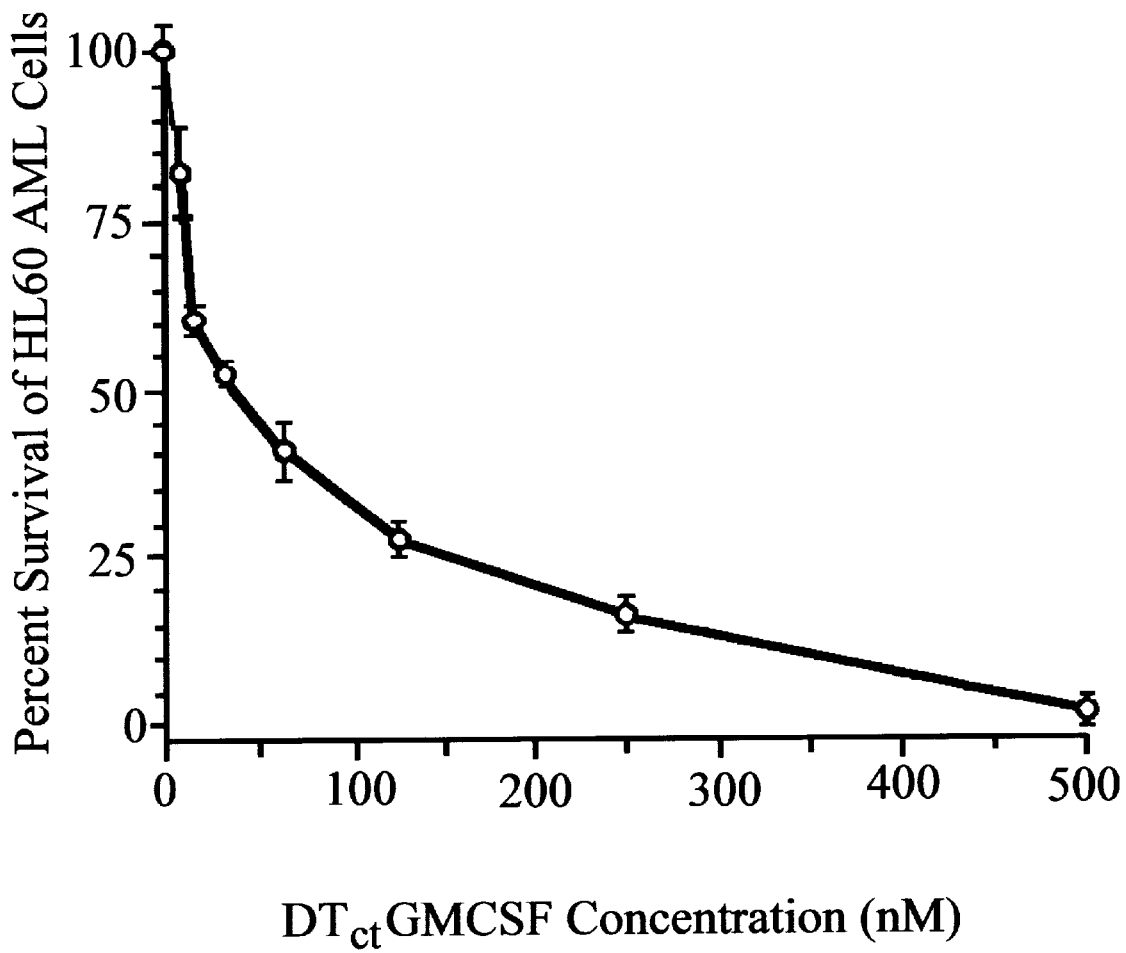
FIG. 6 is a graph showing cytotoxic activity of BEV-derived $DT_{ct}$GMCSF in HL-60 myeloid leukemia cells.

To translate the $OD_{540}$ values into the number of live cells in each well, the $OD_{540}$ values were compared to those of standard $OD_{540}$-versus-cell number curves generated for each cell line. The cytotoxic activity as determined by MTT assay, of $DT_{ct}$GMCSF in relation to the survival of HL-60 myeloid leukemia cells is shown in FIG. 6. The data points represent the mean (±SE) values from 3 independent experiments. The mean IC50 value was 46.3±18.8 nM and the composite survival curve IC50 value was 28.7 nM (a concentration of 100 nM $DT_{ct}$GMCSF is equivalent to approximately 6 μg/ml). The percent survival was calculated using the formula: % survival=Live cell number [test]/Live cell number [control]×100.

Results

Final yields of $DT_{ct}$GMCSF fusion toxin produced in a baculoviral expression system as a cytosolic product were approximately 8–10 mg/L (approximately $10^9$ Sf21 cells). This level of $DT_{ct}$GMCSF expression was approximately 100-fold higher than that achieved using an *E. coli* expression system.

Figure 7A:
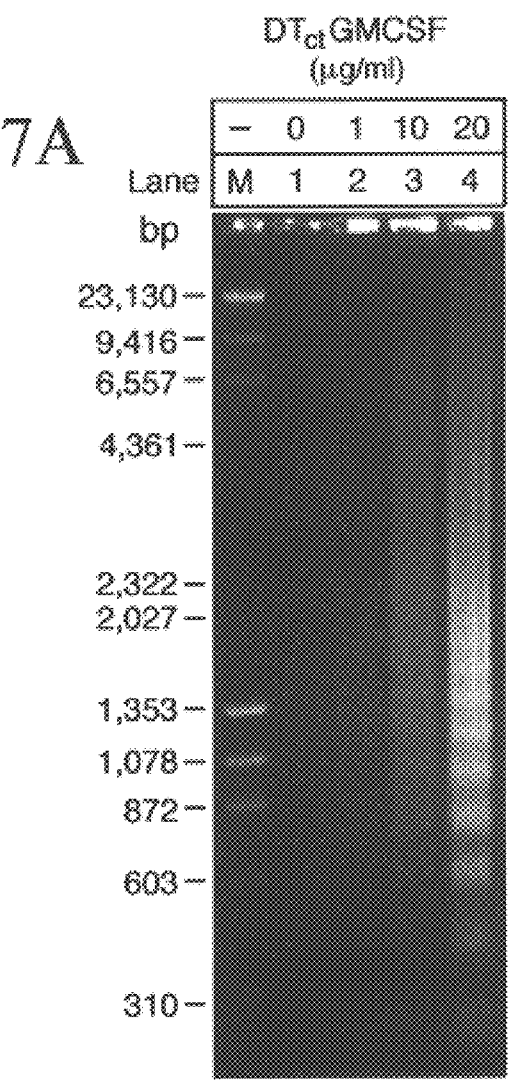
FIG. 7A is a gel showing apoptosis of HL-60 cells exposed to the indicated amounts of $DT_{ct}$GMCSF fusion toxin, as evidenced by a laddering of oligonucleosomal sized DNA fragments.
Figure 7B:
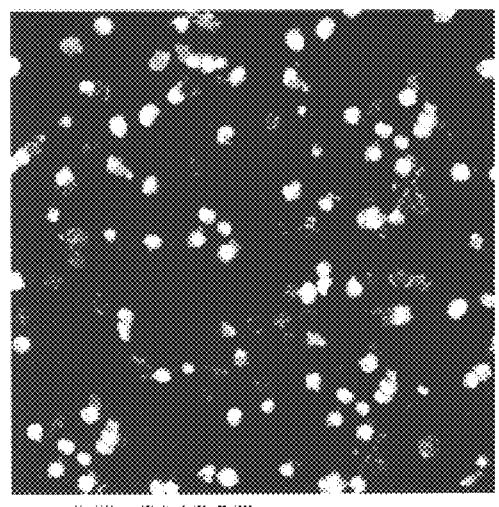
FIG. 7B is a photograph showing apoptosis in untreated, control HL-60 cells.
Figure 7C:
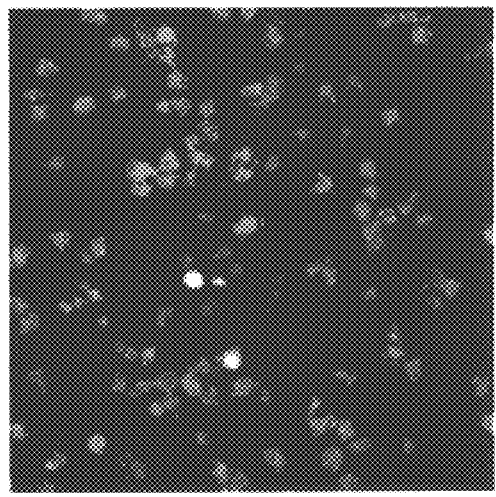
FIG. 7C is a photograph showing apoptosis in $DT_{ct}$GMCSF treated HL-60 cells.
Figure 8A:
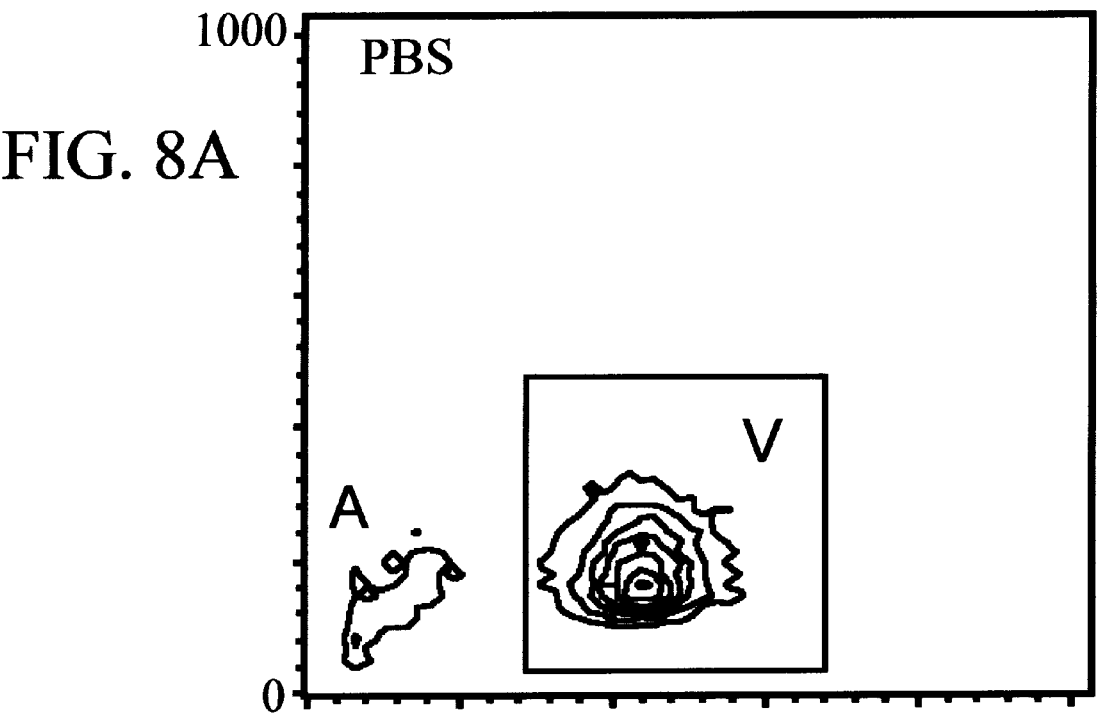
FIGS. 8A–8D show the results of FACS analysis as a function of right angle light scatter of cells treated with $DT_{ct}$GMCSF.
Figure 8B:
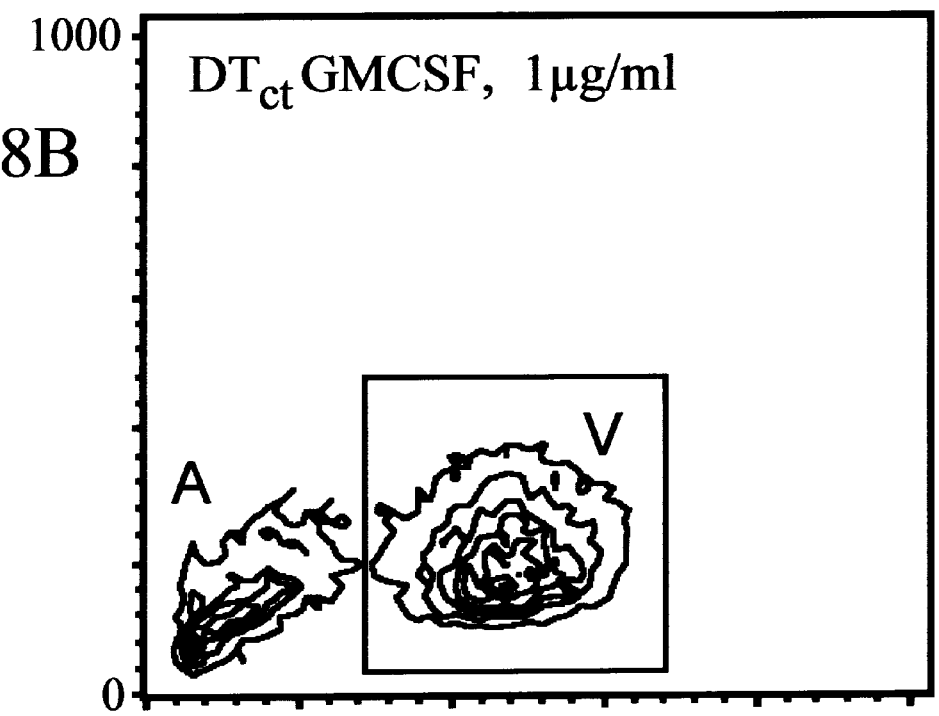
Figure 8C:
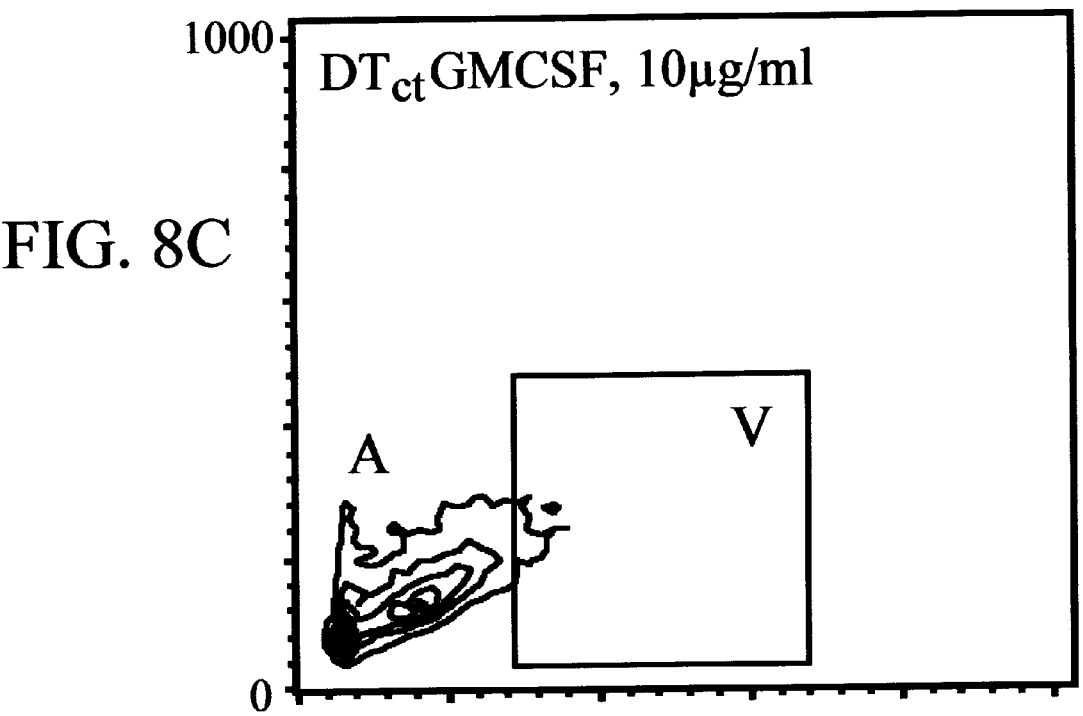
Figure 8D:
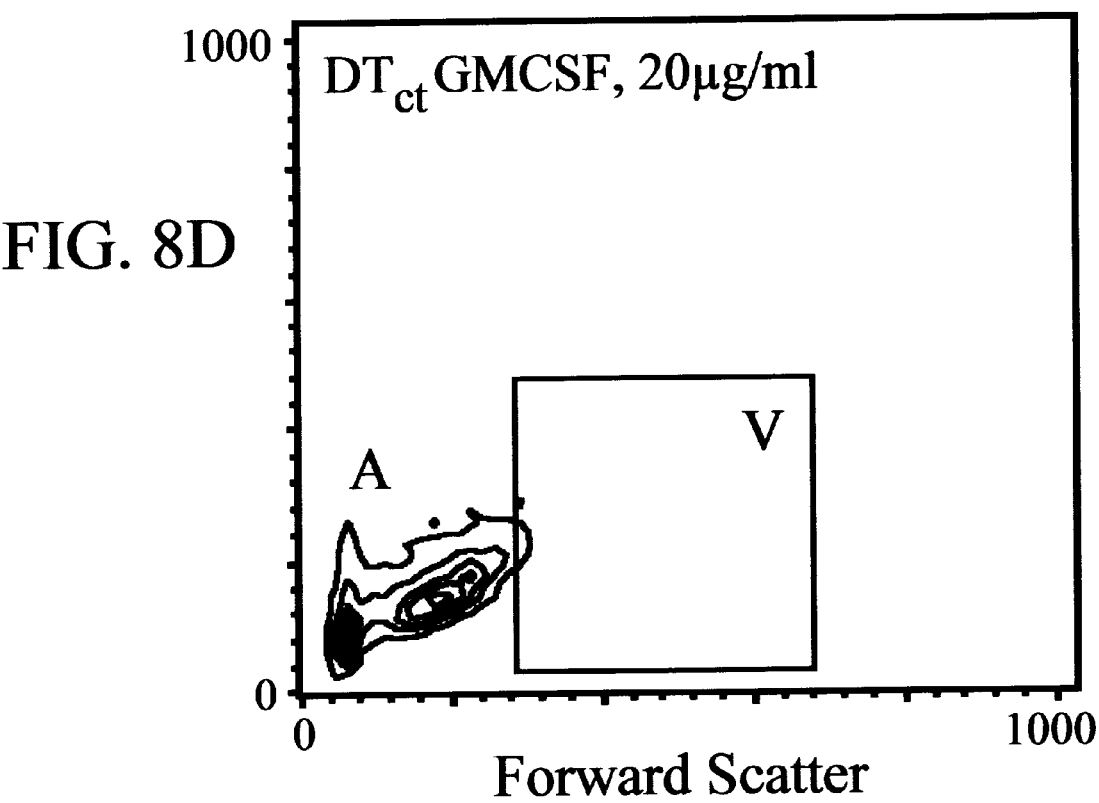
Figure 8E:
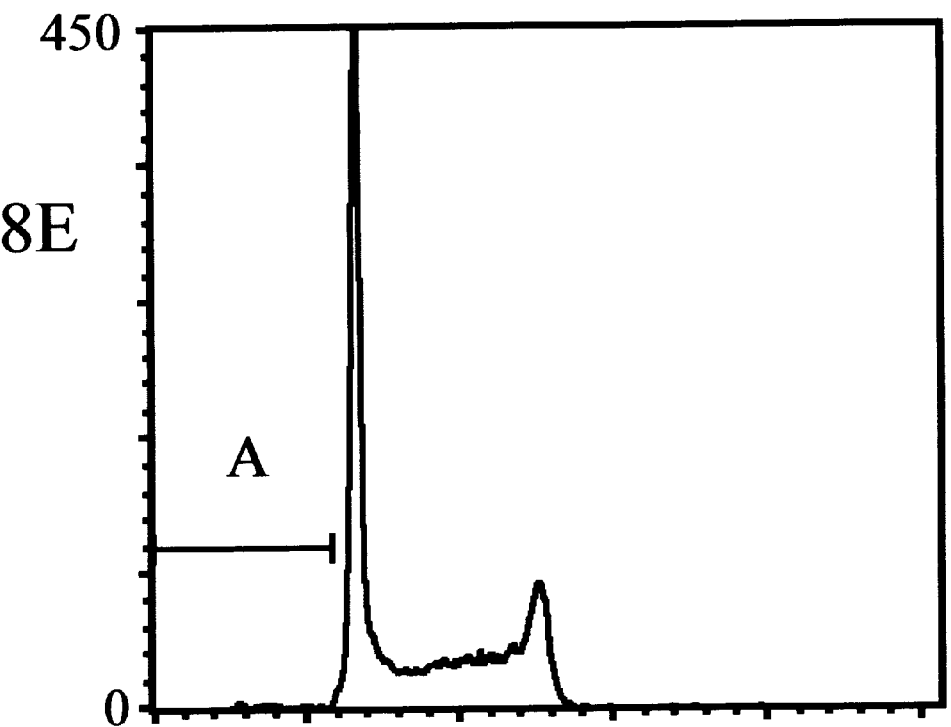
FIGS. 8E–8H show the results of fluorescence analysis as a function of relative cell number of cells treated with $DT_{ct}$GMCSF.
Figure 8F:
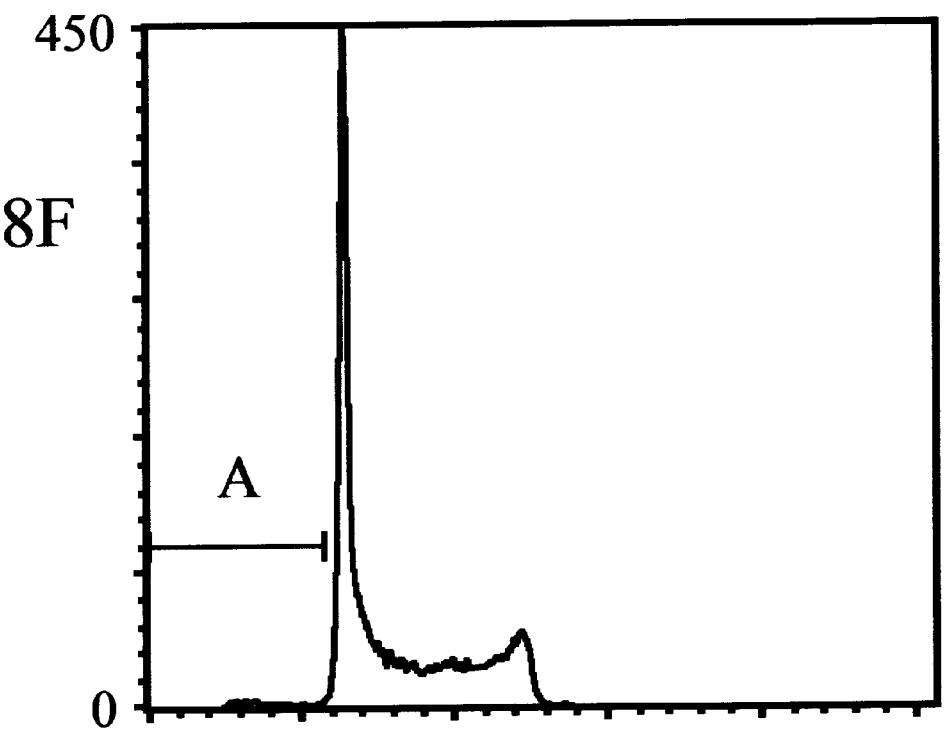
Figure 8G:
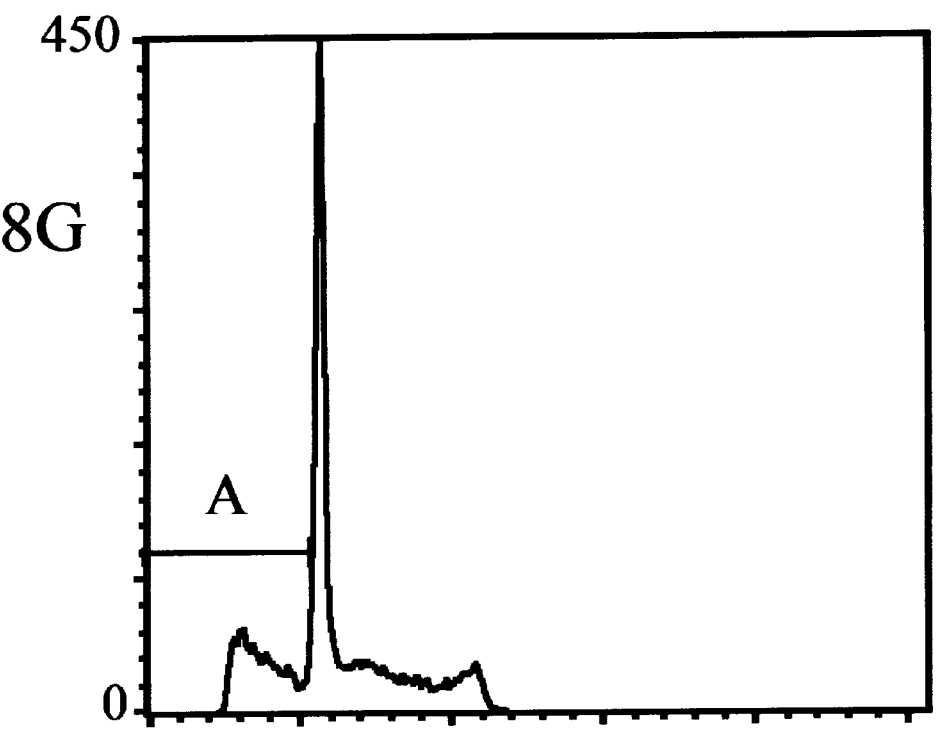
Figure 8H:
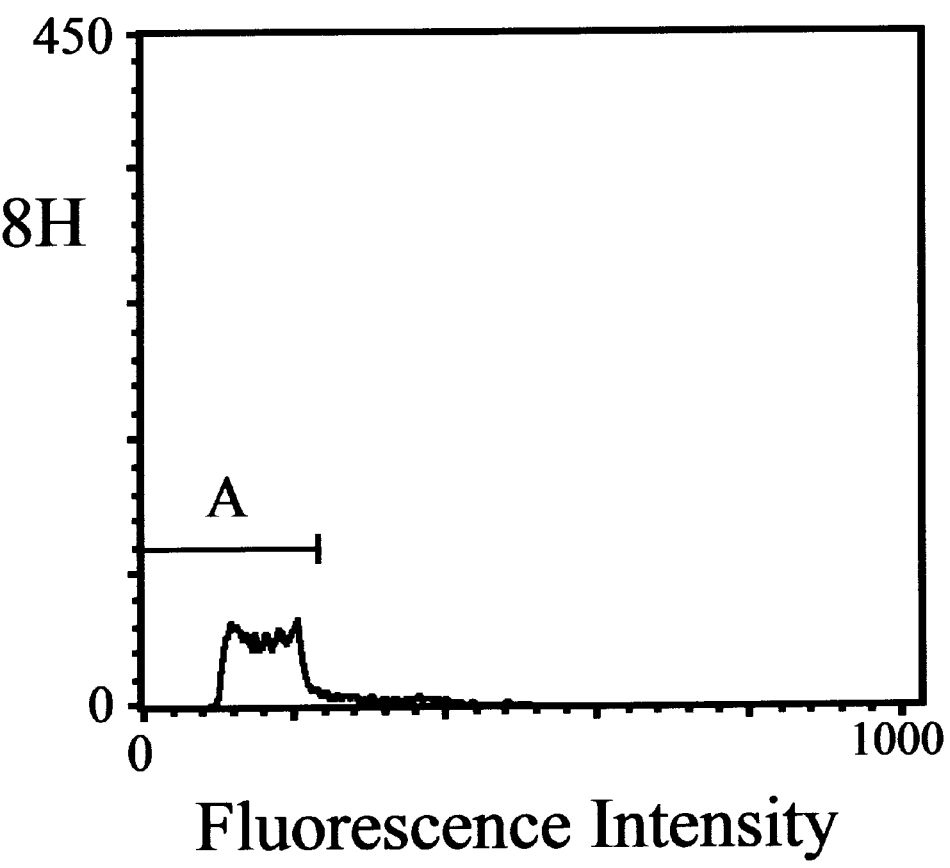

FIG. 7 shows evidence of apoptosis of HL-60 resulting from treatment of the cells with $DT_{ct}$GMCSF. For FIG. 7A, HL-60 myeloid leukemia cells were exposed to varying amounts of the BEVS produced $DT_{ct}$GMCSF fusion toxin for 36 hours. Following this incubation period, DNA from supernatants of Triton X-100 lysates was prepared for analysis of fragmentation as described previously by Uckun, et al., *Science.* 267:886–891, (1995). DNA was fractionated by electrophoresis through 1% agarose gels. Fractionated DNA was then visualized by UV light after being stained with ethidium bromide. The nucleic acid molecular size standard used was a mixture of λ-DNA/HindIII fragments and φX174 DNA/HaeIII fragments (lane M).

The cytotoxic activity of $DT_{ct}$GMCSF was examined against the HL-60 human AML cell line in dose response studies using in vitro MTT assays. As shown in FIG. 5, $DT_{ct}$GMCSF exhibited significant cytotoxicity against the HL-60 human AML cell line in 3 of 3 independent experiments with a mean IC50 value of 46.3±18.8 nM and a composite survival curve IC50 value of 28.7 nM (data not shown).

It will be understood by those skilled in the art that the present invention is not limited to the examples discussed above, but may be changed or modified without departing from the spirit and scope of the invention. All references discussed or cited herein are incorporated herein by reference.

We claim:

1. A process for producing a fusion toxin of $DT_{ct}$ linked to a targeting moiety, comprising the steps of:

expressing a $DT_{ct}$-targeting moiety fusion toxin in insect cells; and isolating the expressed fusion protein.

2. The process of claim 1, wherein the targeting moiety binds a cell surface receptor.

3. The process of claim 1, wherein the targeting moiety is selected from the group consisting of GMCSF, ELF, MSH, IL-2, IL-4, IL-6, and anti-cell surface antibodies.

4. The process of claim 1, wherein the targeting moiety is GMCSF.

5. The process of claim 1, wherein the step of expressing comprises:

transfecting the insect cells with an expression vector encoding a $DT_{ct}$-targeting moiety fusion toxin.

6. The process of claim 5, wherein the expression vector comprises a baculovirus expression vector.

7. The process of claim 1, wherein the insect cells are obtained from an insect of the order Lepidoptera.

8. The process of claim 1, wherein the insect cells are obtained from *Spodoptera frugiperda* or *Trichoplusia ni*.

9. The process of claim 1, wherein the step of isolating comprises ion exchange chromatography at a pH in the range of 3.5 to 4.5.

10. The process of claim 1, wherein the step of isolating comprises solubilizing the fusion toxin from the insect cells in a buffer including a surfactant; and isolating the fusion toxin using ion exchange chromatography at a pH of about 3.5 to 4.5.

11. The process of claim 9, wherein the surfactant is Tergitol NP-40.

12. An expression vector comprising:

a DNA sequence encoding a $DT_{ct}$ fusion toxin; and transcriptional and translational control elements for expression of the DNA sequence in insect cells.

13. The expression vector of claim 12, wherein the encoded fusion toxin includes a targeting moiety for targeting the fusion toxin to a cell or tissue.

14. The expression vector of claim 12, wherein the transcriptional and translational control elements are present in a baculovirus expression system.

15. The expression vector of claim 12, wherein the DNA sequence encodes a $DT_{ct}$GMCSF fusion toxin.

* * * * *

UNITED STATES PATENT AND TRADEMARK OFFICE
CERTIFICATE OF CORRECTION

PATENT NO.   : 6,168,932 B1
DATED        : January 2, 2001
INVENTOR(S)  : Fatih M. Uckun et al.

It is certified that error appears in the above-identified patent and that said Letters Patent is hereby corrected as shown below:

Column 5,
Line 22, "reside" should read -- residue --

Column 7,
Line 6, "oxin" should read -- toxin --
Line 21, "gentamicin" should read -- gentamycin --

Column 10,
Line 60, "Commassie blue" should read -- Coomassie Blue --

Column 16,
Line 51, "claim 9" should read -- claim 10 --.

Signed and Sealed this

Thirteenth Day of August, 2002

*Attest:*

*Attesting Officer*

JAMES E. ROGAN
*Director of the United States Patent and Trademark Office*